US 6,566,381 B1
United States Patent
Cheng et al.

(10) Patent No.: US 6,566,381 B1
(45) Date of Patent: May 20, 2003

(54) HETERO-SUBSTITUTED METALLOPROTEASE INHIBITORS

(75) Inventors: Menyan Cheng, West Chester, OH (US); Neil Gregory Almstead, Loveland, OH (US); Michael George Natchus, Glendale, OH (US); Stanislaw Pikul, Mason, OH (US); Biswanath De, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/516,743

(22) Filed: Mar. 1, 2000

Related U.S. Application Data

(60) Provisional application No. 60/122,718, filed on Mar. 3, 1999.

(51) Int. Cl.[7] ............... A61K 31/42; A61K 31/4164; A61K 31/35; A61K 31/34; C07D 277/20

(52) U.S. Cl. ............. 514/365; 514/183; 514/256; 514/277; 514/385; 514/396; 514/451; 544/242; 544/335; 546/1; 548/182; 548/186; 548/187; 548/189; 549/356; 549/426; 549/427; 549/429; 549/491; 549/498

(58) Field of Search ............... 548/182, 186, 548/187, 189; 549/35.6, 426, 427; 544/242, 335; 546/1; 514/365, 183, 256, 277, 385, 396, 451, 461

(56) References Cited

U.S. PATENT DOCUMENTS

| | | | |
|---|---|---|---|
| 5,310,763 A | 5/1994 | Campion et al. | |
| 5,442,110 A | 8/1995 | Isomura et al. | 562/261 |
| 5,455,258 A | 10/1995 | MacPherson et al. | 514/357 |
| 5,506,242 A | 4/1996 | MacPherson et al. | 514/336 |
| 5,534,541 A | 7/1996 | Drauz et al. | 514/448 |
| 5,552,419 A | 9/1996 | MacPherson et al. | 514/357 |
| 5,563,151 A | 10/1996 | Bowles et al. | |
| 5,756,545 A * | 5/1998 | Michael et al. | 514/729 |

FOREIGN PATENT DOCUMENTS

| | | |
|---|---|---|
| DE | 1985184 * | 7/1999 |
| EP | 0 498 665 | 8/1992 |
| EP | 0 606 046 | 7/1994 |
| EP | 0 757 037 | 2/1997 |
| EP | 0 877 018 | 11/1998 |
| EP | 877019 | 11/1998 |
| EP | 0 877 019 | 11/1998 |
| EP | 0 915 086 | 5/1999 |
| EP | 0 950 656 | 10/1999 |
| EP | 967201 * | 12/1999 |
| JP | 10 204054 | 8/1998 |
| JP | 11246527 * | 9/1999 |
| WO | WO 92/17460 | 10/1992 |
| WO | WO 93/00082 | 1/1993 |
| WO | WO 95/35275 | 12/1995 |
| WO | WO 96/33172 | 10/1996 |
| WO | 9637492 * | 11/1996 |
| WO | WO 97/05865 | 2/1997 |
| WO | WO 97/20824 | 6/1997 |
| WO | WO 97/25315 | 7/1997 |
| WO | 9727174 * | 7/1997 |
| WO | WO 97/32846 | 9/1997 |
| WO | WO 98/00825 | 3/1998 |
| WO | WO 98/08814 | 3/1998 |
| WO | WO 98/08815 | 3/1998 |
| WO | WO 98/08822 | 3/1998 |
| WO | WO 98/08823 | 3/1998 |
| WO | WO 98/08827 | 3/1998 |
| WO | WO 98/08850 | 3/1998 |
| WO | WO 98/17645 | 4/1998 |
| WO | WO 98/31664 | 7/1998 |
| WO | WO 98/33768 | 8/1998 |
| WO | WO 98/42659 | 10/1998 |
| WO | WO 98/43963 | 10/1998 |
| WO | WO 98/50348 | 11/1998 |
| WO | WO 99/06340 | 2/1999 |
| WO | 9932150 * | 7/1999 |
| WO | WO 99/42443 | 8/1999 |
| WO | 9942443 * | 8/1999 |
| WO | WO 99/51572 | 10/1999 |
| WO | 2000035492 * | 6/2000 |

OTHER PUBLICATIONS

Pitts W.J.et al."JMed. Chem." 43/1, pp.2730, Isoxazolines as pot. antagonist (Jan. 2000).*

Kahl, J.U. et al., "Synthesis of Two Naturally Occuring Diastereomeric Dihydroxyprolines: 2,3–trans–3,4–Dihydroxy–l–proline and 2,3–cis–3,4–trans–3,4–Dihydroxy–l–proline", Liebigs Ann. Chem., 1981, pp. 1445–1450.

Hudson, C.B. et al., "On the Synthesis of 3,4–Dihydroxyprolines i. Cis–Glyolation of 3,4–Dehydroproline Derivatives", Aust. J. Chem., vol. 21, 1968, pp. 769–782.

(List continued on next page.)

Primary Examiner—Richard L. Raymond
Assistant Examiner—Sudhaker B. Patel
(74) Attorney, Agent, or Firm—David V. Upite; Carl J. Roof

(57) ABSTRACT

Heterocyclic substituted compounds having the general structure:

(I)

which are inhibitors of metalloproteases and which are effective in treating conditions characterized by excess activity of these enzymes.

21 Claims, No Drawings

OTHER PUBLICATIONS

Andreatta, R.H., "Synthesis of Cis and Trans Isomers of 4–Chloro–Proline, 4–Bromo–$_L$–Proline and 4–Amino–$_L$–Proline", *Aust. J. Chem.*, vol. 20, 1967, pp. 1493–1509.

Heintzelman, G.R. et al., "Imino Diels–Alder–Based Construction of a Piperidine A–Ring Unit for Total Synthesis of the Marine Hepatotoxin Cylindrospermopsin", *Chemical Abstracts*, vol. 125, No. 5, 1996, Abstract No. 58826.

Herdeis, C., et al., "Amino Acids. XII. (±)–Pipecolic Acid Derivatives. Part 2. An Expedient Synthetic Entry to Substituted Pipecolic Acids", *Chemical Abstracts*, vol. 117, No. 17, 1992, Abstract No. 171989.

Natelson, S. "Preparation of D–, DL–, and L–Homoserine Lactone from Methionine", *Microchemical Journal*, vol. 40, 1989, pp. 226–232.

Hansel, J.G. et al., "Oxazoline Formation via a Palladium–catalyzed Cyclization: A Direct, Stereoselective Approach to cis–5–Amino–2–cyclopenten–1–ol Derivatives", *Tetrahedron Letters*, vol. 36, No. 17, 1995, pp. 2913–2916.

Sarras, M.P., "BMP–1 and the Astacin Family of Metalloproteinases: a Potential Link Between the Extracellular Matrix, Growth Factors, and Pattern Formation", *BioEssays*, vol. 18, No. 6, 1996 (Abstract attached).

Yoneda, N., et al., "Reaction of L–alpha–tosylamido–beta–propiolactone I. Synthesis Reactions with Amines, and Derivation to L–serine", *Yakugaku Zasshi*, vol. 89, No. 1, 1969 (Abstract attached).

Johnson, W.H., et al., "Collagenase Inhibitors: Their Design and Potential Therapeutic Use", *J. Enzyme Inhibition*, vol. 2, 1987, pp. 1–22.

Schwartz, M.A., et al., "8 Synthesis Inhibitors of Bacterial and Mammalian Interstitial Collagenases", *Progress in Medicinal Chemistry*, vol. 29, 1992, pp. 271–334.

Singh, J., et al., "Relationship Between Structure and Bioavailability in a Series of Hydroxamate Based Metalloprotease Inhibitors", *Bioorganic & Medicinal Chemistry Letters*, vol. 5, No. 4, 1995, pp. 337–342.

Tomczuk, B.E., et al., "Hyrdoxamate Inhibitors of the Matrix Metallo–Proteinases (MMPs) Containing Novel $P_1^1$ Heteroatom Based on Modifications", *Bioorganic & Medicinal Chemistry Letters*, vol. 5, No. 4, 1995, pp. 343–348.

Chapman, K.T., et al., "Inhibition of Matrix Metalloproteinases by N–Carboxyalkyl Peptides", *J. Med. Chem.*, vol. 36, 1993, pp. 429–4301.

Turbanti, L., et al., "1,2–Cyclomethylenecarboxylic Monoamide Hydroxamic Derivatives. A Novel Class of Non–Amino Acid Angiotensin Converting Enzyme Inhibitors", *J. Med. Chem.*, vol. 36, 1993, pp. 699–707.

Yamani et al PubMed Abstr.:11997283;Circulation 2002 Apr. 23;105/16:1955–61.

Cai et al(PubMed Abstr.;1148127;Clin Cancer Res. 2002 Apr.;8/4, 1152–6.

Halis et al(PubMed Abstr.:11861412;Cird Res 2002 Feb. 22;90/3:251–62.

* cited by examiner

HETERO-SUBSTITUTED METALLOPROTEASE INHIBITORS

CROSS REFERENCE TO RELATED APPLICATION

This application claims the benefit of U.S. Provisional Application No. 60/122,718, filed Mar. 3, 1999.

TECHNICAL FIELD

This invention is directed to compounds which are useful in treating diseases associated with metalloprotease activity, particularly zinc metalloprotease activity. The invention is also directed to pharmaceutical compositions comprising the compounds, and to methods of treating metalloprotease-related maladies using the compounds or the pharmaceutical compositions.

BACKGROUND

A number of structurally related metalloproteases effect the breakdown of structural proteins. These metalloproteases often act on the intercellular matrix, and thus are involved in tissue breakdown and remodeling. Such proteins are referred to as metalloproteases or MPs.

There are several different families of MPs, classified by sequence homology, disclosed in the art. These MPs include Matrix-Metallo Proteases (MMPs); zinc metalloproteases; many of the membrane bound metalloproteases; TNF converting enzymes; angiotensin-converting enzymes (ACEs); disintegrins, including ADAMs (see Wolfsberg et al, 131 *J. Cell Bio.* 275–78 Oct., 1995); and the enkephalinases. Examples of MPs include human skin fibroblast collagenase, human skin fibroblast gelatinase, human sputum collagenase, aggrecanse and gelatinase, and human stromelysin. Collagenases, stromelysin, aggrecanase and related enzymes are thought to be important in mediating the symptomatology of a number of diseases.

Potential therapeutic indications of MP inhibitors have been discussed in the literature. See, for example, U.S. Pat. No. 5,506,242 (Ciba Geigy Corp.) and U.S. Pat. No. 5,403,952 (Merck & Co.); the following PCT published applications: WO 96/06074 (British Bio Tech Ltd.); WO 96/00214 (Ciba Geigy), WO 95/35275 (British Bio Tech Ltd.), WO 95/35276 (British Bio Tech Ltd.), WO 95/33731 (Hoffman-LaRoche), WO 95/33709 (Hoffman-LaRoche), WO 95/32944 (British Bio Tech Ltd.), WO 95/26989 (Merck), WO 5 9529892 (DuPont Merck), WO 95/24921 (Inst. Opthamology), WO 95/23790 (SmithKline Beecham), WO 95/22966 (Sanofi Winthrop), WO 95/19965 (Glycomed), WO 95 19956 (British Bio Tech Ltd), WO 95/19957 (British Bio Tech Ltd.), WO 95/19961 (British Bio Tech Ltd.), WO 95/13289 (Chiroscience Ltd.), WO 95/12603 (Syntex), WO 95/09633 (Florida State Univ.), WO 95/09620 (Florida State Univ.), WO 95/04033 (Celitech), WO 94/25434 (Celitech), WO 94/25435 (Celltech); WO 93/14112 (Merck), WO 94/0019 (Glaxo), WO 93/21942 (British Bio Tech Ltd.), WO 92/22523 (Res. Corp. Tech Inc.), WO 94/10990 (British Bio Tech Ltd.), WO 93/09090 (Yamanouchi); British patents GB 2282598 (Merck) and GB 2268934 (British Bio Tech Ltd.); published European Patent Applications EP 95/684240 (Hoffman LaRoche), EP 574758 (Hoffman LaRoche) and EP 575844 (Hoffman LaRoche); published Japanese applications JP 08053403 (Fujusowa Pharm. Co. Ltd.) and JP 7304770 (Kanebo Ltd.); and Bird et al., *J. Med. Chem.*, vol. 37, pp. 158–69 (1994).

Examples of potential therapeutic uses of MP inhibitors include rheumatoid arthritis—Mullins, D. E., et al., *Biochim. Biophys. Acta.* (1983) 695:117–214; osteoarthritis—Henderson, B., et al., *Drugs of the Future* (1990) 15:495–508; cancer—Yu, A. E. et al., Matrix Metalloproteinases—Novel Targets for Directed Cancer Therapy, *Drugs & Aging*, Vol. 11(3), p. 229–244 (September 1997), Chambers, A. F. and Matrisian, L. M., Review: Changing Views of the Role of Matrix Metalloproteinases in Metastasis, *J. of the Nat'l Cancer Inst.*, Vol. 89(17), p. 1260–1270 (September 1997), Bramhall, S. R., The Matrix Metalloproteinases and Their Inhibitors in Pancreatic Cancer, *Internat'l J. of Pancreatology*, Vol. 4, p. 1101–1109 (May 1998), Nemunaitis, J. et al., Combined Analysis of Studies of the Effects of the Matrix Metalloproteinase Inhibitor Marimastat on Serum Tumor Markers in Advanced Cancer: Selection of a Biologically Active and Tolerable Dose for Longer-term Studies, *Clin. Cancer Res.*, Vol 4, p. 1101–1109 (May 1998), and Rasmussen, H. S. and McCann, P. P, Matrix Metalloproteinase Inhibition as a Novel Anticancer Strategy: A Review with Special Focus on Batimastat and Marimastat, *Pharmacol. Ther.*, Vol 75(1), p. 69–75 (1997); the metastasis of tumor cells—ibid, Broadhurst, M. J., et al., European Patent Application 276,436 (published 1987), Reich, R., et al., *Cancer Res.*, Vol. 48, p. 3307–3312 (1988); multiple sclerosis—Gijbels et al., *J. Clin. Invest.*, vol. 94, p. 2177–2182 (1994); and various ulcerations or ulcerative conditions of tissue. For example, ulcerative conditions can result in the cornea as the result of alkali burns or as a result of infection by *Pseudomonas aeruginosa*, Acanthamoeba, Herpes simplex and vaccinia viruses. Other examples of conditions characterized by undesired metalloprotease activity include periodontal disease, epidermolysis bullosa, fever, inflammation and scleritis (e.g., DeCicco et al., PCT published application WO 95/29892, published Nov. 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa et al.; U.S. Pat. No. 4,771,038, issued Sep. 13, 1988 to Wolanin et al.; U.S. Pat. No. 4,743,587, issued May 10, 1988 to Dickens et al., European Patent Publication No. 575,844, published Dec. 29, 1993 by Broadhurst et al.; International Patent Publication No. WO 93/09090, published May 13, 1993 by Isomura et al.; World Patent Publication 92/17460, published Oct. 15, 1992 by Markwell et al.; and European Patent Publication No. 498,665, published Aug. 12, 1992 by Beckett et al.

It would be advantageous to inhibit these metalloproteases in treating diseases related to unwanted metalloprotease activity. Though a variety of MP inhibitors have been prepared, there is a continuing need for potent matrix metalloprotease inhibitors useful in treating diseases associated with metalloprotease activity.

SUMMARY OF THE INVENTION

The invention provides compounds which are potent inhibitors of metalloproteases and which are effective in treating conditions characterized by excess activity of these enzymes. In particular, the present invention relates to compounds having a structure according to the following Formula (I):

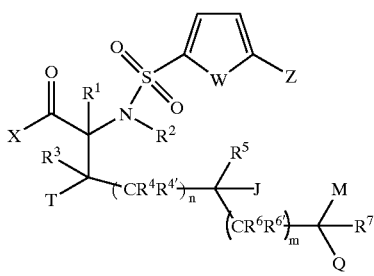

(I)

where J, M, Q, T, W, X, Z, $R^1$, $R^2$, $R^3$, $R^4$, $R^{4'}$, $R^5$, $R^6$, $R^{6'}$, $R^7$, m, and n have the meanings described in the Detailed Description section below. This invention also includes optical isomers, diastereomers and enantiomers of the formula above, and pharmaceutically-acceptable salts, biohydrolyzable amides, esters, and imides thereof.

The compounds of the present invention are useful for the treatment of diseases and conditions which are characterized by unwanted metalloprotease activity. Accordingly, the invention further provides pharmaceutical compositions comprising these compounds. The invention still further provides methods of treatment for metalloprotease-related maladies.

DETAILED DESCRIPTION OF THE INVENTION

I. Terms and Definitions

The following is a list of definitions for terms used herein:
The following is a list of definitions for terms used herein.

"Acyl" or "carbonyl" is a radical formed by removal of the hydroxy from a carboxylic acid (i.e., R—C(=O)—). Preferred acyl groups include (for example) acetyl, formyl, and propionyl.

"Alkyl" is a saturated hydrocarbon chain having 1 to 15 carbon atoms, preferably 1 to 10, more preferably 1 to 4 carbon atoms. "Alkene" is a hydrocarbon chain having at least one (preferably only one) carbon-carbon double bond and having 2 to 15 carbon atoms, preferably 2 to 10, more preferably 2 to 4 carbon atoms. "Alkene" is a hydrocarbon chain having at least one (preferably only one) carbon-carbon triple bond and having 2 to 15 carbon atoms, preferably 2 to 10, more preferably 2 to 4 carbon atoms. Alkyl, alkene and alkyne chains (referred to collectively as "hydrocarbon chains") may be straight or branched and may be unsubstituted or substituted. Preferred branched alkyl, alkene and alkyne chains have one or two branches, preferably one branch. Preferred chains are alkyl. Alkyl, alkene and alkyne hydrocarbon chains each may be unsubstituted or substituted with from 1 to 4 substituents; when substituted, preferred chains are mono-, di-, or tri-substituted. Alkyl, alkene and alkyne hydrocarbon chains each may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred hydrocarbon groups include methyl, ethyl, propyl, isopropyl, butyl, vinyl, allyl, butenyl, and exomethylenyl.

Also, as referred to herein, a "lower" alkyl, alkene or alkyne moiety (e.g., "lower alkyl") is a chain comprised of 1 to 6, preferably from 1 to 4, carbon atoms in the case of alkyl and 2 to 6, preferably 2 to 4, carbon atoms in the case of alkene and alkyne.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms, in the ring. Bicyclic aryl rings include ring systems wherein one ring is aryl and the other ring is aryl, cycloalkyl, or heterocycloalkyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Preferred aryl rings include naphthyl, tolyl, xylyl, and phenyl. The most preferred aryl ring radical is phenyl.

"Aryloxy" is an oxygen radical having an aryl substituent (i.e., —O-aryl). Preferred aryloxy groups include (for example) phenoxy, napthyloxy, methoxyphenoxy, and methylenedioxyphenoxy.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms, in the ring. Bicyclic cycloalkyl rings contain from 7 to 17 carbon atoms, preferably from 7 to 12 carbon atoms, in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be substituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" or "halogen" is fluoro, chloro, bromo or iodo. Preferred halo are fluoro, chloro and bromo; more preferred typically are chloro and fluoro, especially fluoro.

"Haloalkyl" is a straight, branched, or cyclic hydrocarbon substituted with one or more halo substituents. Preferred are $C_1$–$C_{12}$ haloalkyls; more preferred are $C_1$–$C_6$ haloalkyls; still more preferred still are $C_1$–$C_3$ haloalkyls. Preferred halo substituents are fluoro and chloro. The most preferred haloalkyl is trifluoromethyl.

"Heteroatom" is a nitrogen, sulfur, or oxygen atom. Groups containing more than one heteroatom may contain different heteroatoms.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more to preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more carbon-carbon double bonds and/or one or more carbon-carbon triple bonds. Preferred unsaturated heteroalkyls have one or two double bonds or one triple bond, more preferably one double bond. Heteroalkyl chains may be unsubstituted or substituted with from 1 to 4 substituents. Preferred substituted heteroalkyl are mono-, di-, or tri-substituted. Heteroalkyl may be substituted with lower alkyl, haloalkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroaryl" is an aromatic ring containing carbon atoms and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably 5 or 6 member atoms, in the ring. Bicyclic heteroaryl rings contain from 8 to 17 member atoms, preferably 8 to 12 member atoms, in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, alkoxy, aryloxy, heteroaryloxy, or any combination thereof. Preferred heteroaryl rings include, but are not limited to, the following:

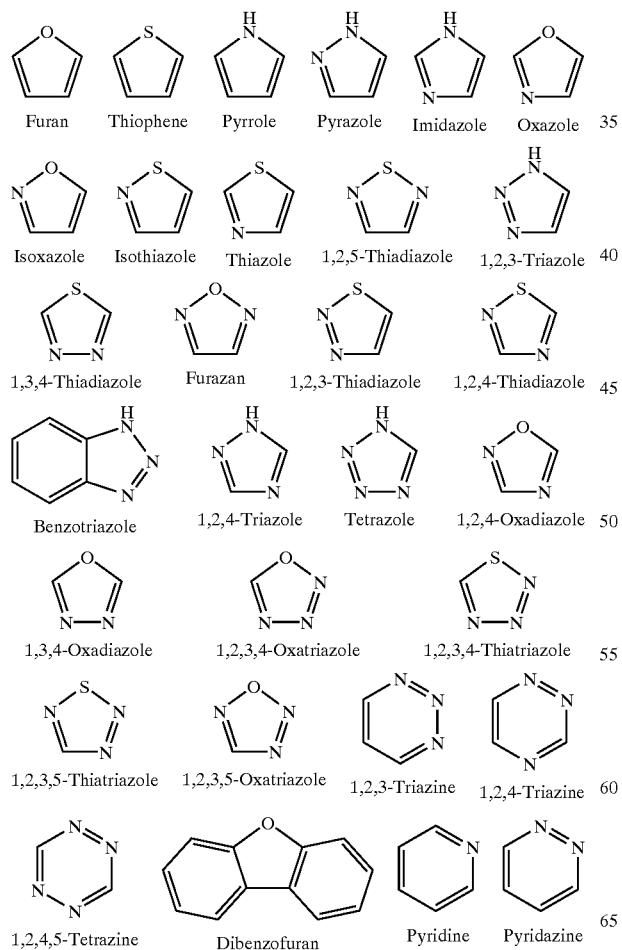

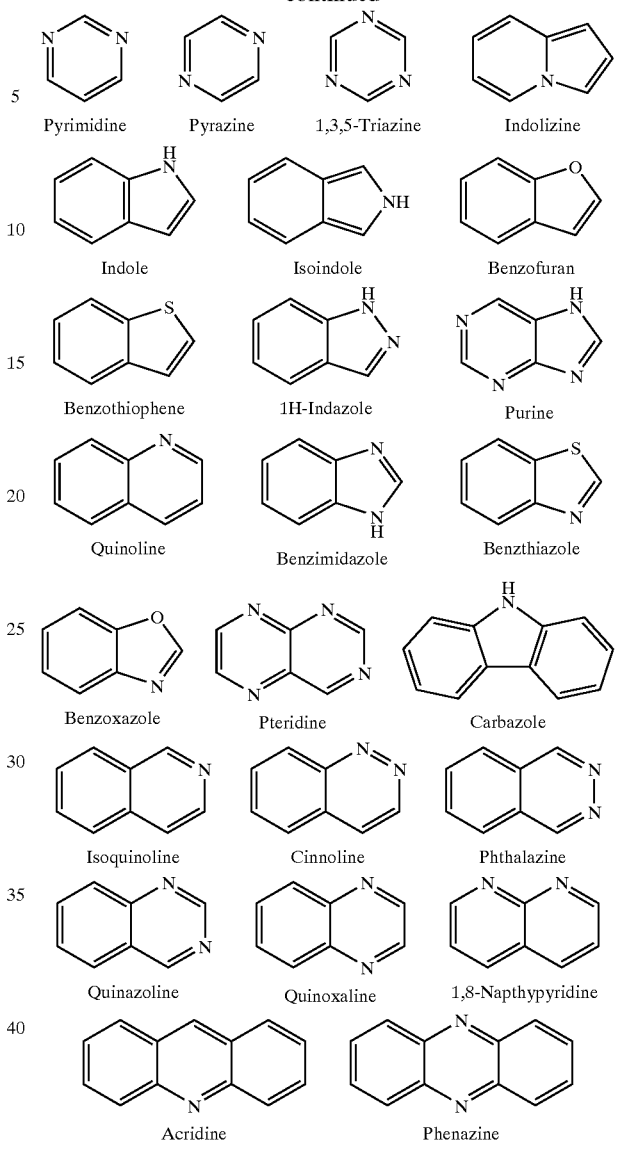

"Heteroaryloxy" is an oxygen radical having a heteroaryl substituent (i.e., —O-heteroaryl). Preferred heteroaryloxy groups include (for example) pyridyloxy, furanyloxy, (thiophene)oxy, (oxazole)oxy, (thiazole)oxy, (isoxazole)oxy, pyrmidinyloxy, pyrazinyloxy, and benzothiazolyloxy.

"Heterocycloalkyl" is a saturated or unsaturated ring containing carbon atoms and from 1 to about 4 (preferably 1 to 3) heteroatoms in the ring. Heterocycloalkyl rings are not aromatic. Heterocycloalkyl rings are monocyclic, or are fused, bridged, or spiro bicyclic ring systems. Monocyclic heterocycloalkyl rings contain from about 3 to about 9 member atoms (carbon and heteroatoms), preferably from 5 to 7 member atoms, in the ring. Bicyclic heterocycloalkyl rings contain from 7 to 17 member atoms, preferably 7 to 12 member atoms, in the ring. Bicyclic heterocycloalkyl rings contain from about 7 to about 17 ring atoms, preferably from 7 to 12 ring atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, alkoxy, aryloxy or any combination thereof. Preferred substituents on heterocycloalkyl include halo and haloalkyl. Preferred heterocycloalkyl rings include, but are not limited to, the following:

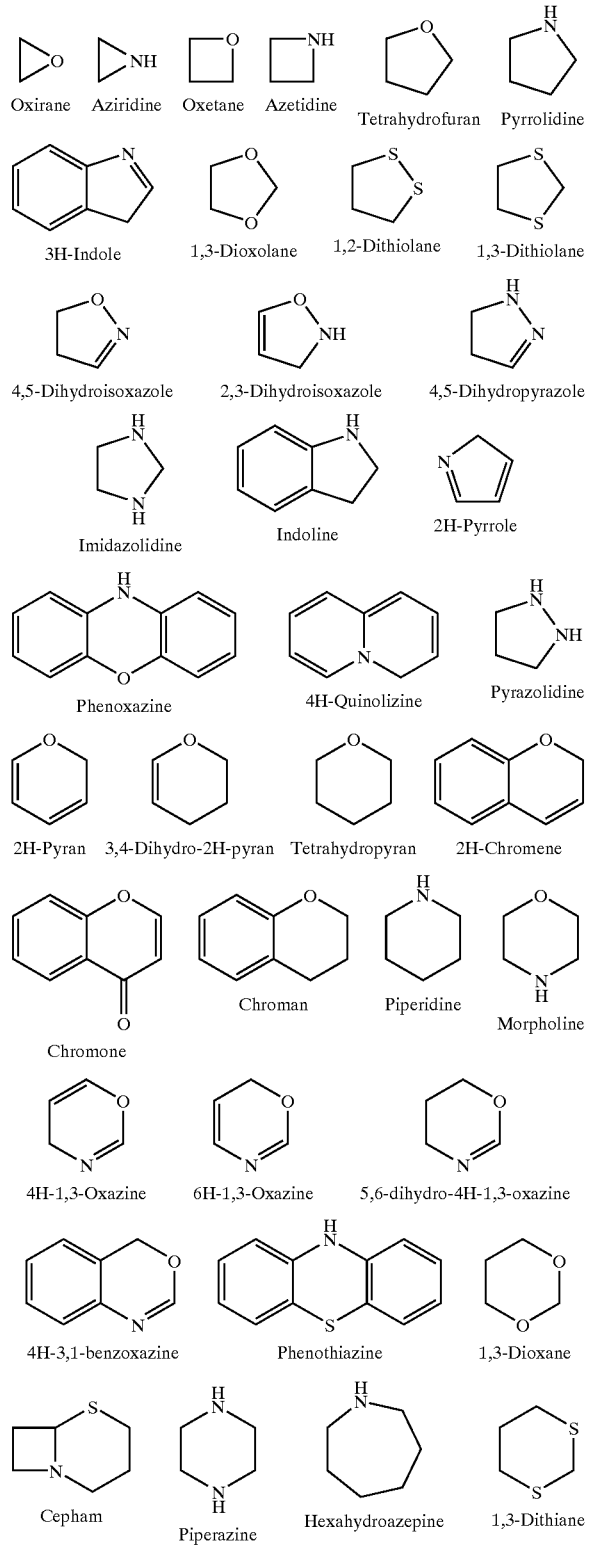

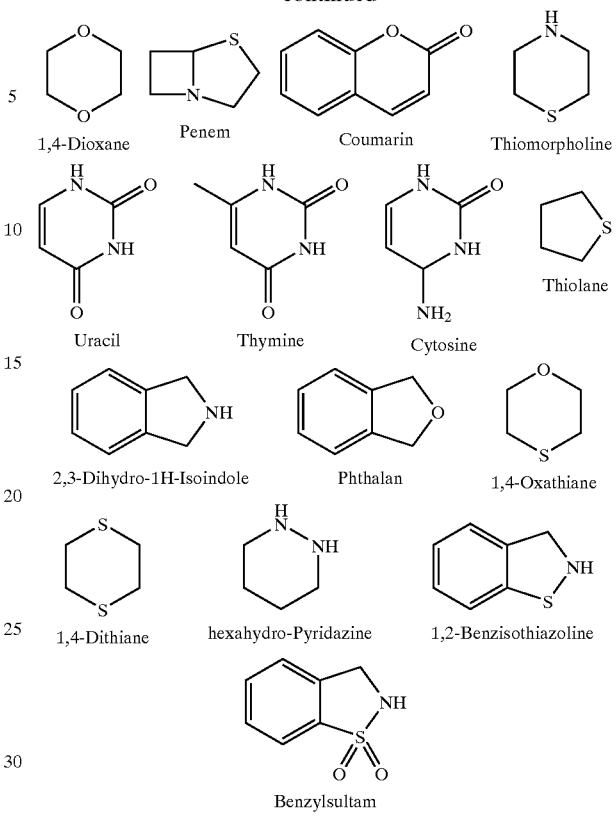

As used herein, "mammalian metalloprotease" refers to the proteases disclosed in the "Background" section of this application. The compounds of the present invention are preferably active against "mammalian metalloproteases", including any metal-containing (preferably zinc-containing) enzyme found in animal, preferably mammalian, sources capable of catalyzing the breakdown of collagen, gelatin or proteoglycan under suitable assay conditions. Appropriate assay conditions can be found, for example, in U.S. Pat. No. 4,743,587, which references the procedure of Cawston, et al., *Anal. Biochem.* (1979) 99:340–345; use of a synthetic substrate is described by Weingarten, H., et al., *Biochem. Biophy. Res. Comm.* (1984) 139:1184–1187. See also Knight, C. G. et al., "A Novel Coumarin-Labelled Peptide for Sensitive Continuous Assays of the Matrix Metalloproteases", *FEBS Letters*, Vol. 296, pp. 263–266 (1992). Any standard method for analyzing the breakdown of these structural proteins can, of course, be used. The present compounds are more preferably active against metalloprotease enzymes that are zinc-containing proteases which are similar in structure to, for example, human stromelysin or skin fibroblast collagenase. The ability of candidate compounds to inhibit metalloprotease activity can, of course, be tested in the assays described above. Isolated metalloprotease enzymes can be used to confirm the inhibiting activity of the invention compounds, or crude extracts which contain the range of enzymes capable of tissue breakdown can be used.

"Spirocycle" is an alkyl or heteroalkyl diradical substituent of alkyl or heteroalkyl wherein said diradical substituent is attached geminally and wherein said diradical substituent forms a ring, said ring containing 4 to 8 member atoms (carbon or heteroatom), preferably 5 or 6 member atoms.

While alkyl, heteroalkyl, cycloalkyl, and heterocycloalkyl groups may be substituted with hydroxy, amino, and amido groups as stated above, the following are not envisioned in the invention:

1. Enols (OH attached to a carbon bearing a double bond).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

A "pharmaceutically-acceptable salt" is a cationic salt formed at any acidic (e.g., hydroxamic or carboxylic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "biohydrolyzable amide" is an amide of a hydroxamic acid-containing (i.e., $R_1$ in Formula (1) is —NHOH) metalloprotease inhibitor that does not interfere with the inhibitory activity of the compound, or that is readily converted in vivo by an animal, preferably a mammal, more preferably a human subject, to yield an active metalloprotease inhibitor. Examples of such amide derivatives are alkoxyamides, where the hydroxyl hydrogen of the hydroxamic acid of Formula (1) is replaced by an alkyl moiety, and acyloxyamides, where the hydroxyl hydrogen is replaced by an acyl moiety (i.e., R—C(=O)—).

A "biohydrolyzable hydroxy imide" is an imide of a hydroxamic acid-containing metalloprotease inhibitor that does not interfere with the metalloprotease inhibitory activity of these compounds, or that is readily converted in vivo by an animal, preferably a mammal, more preferably a human subject to yield an active metalloprotease inhibitor. Examples of such imide derivatives are those where the amino hydrogen of the hydroxamic acid of Formula (1) is replaced by an acyl moiety (i.e., R—C (=O)—).

A "biohydrolyzable ester" is an ester of a carboxylic acid-containing (i.e., $R_1$ in Formula (I) is —OH) metalloprotease inhibitor that does not interfere with the metalloprotease inhibitory activity of these compounds or that is readily converted by an animal to yield an active metalloprotease inhibitor. Such esters include lower alkyl esters, lower acyloxy-alkyl esters (such as acetoxymethyl, acetoxyethyl, aminocarbonyloxymethyl, pivaloyloxymethyl and pivaloyloxyethyl esters), lactonyl esters (such as phthalidyl and thiophthalidyl esters), lower alkoxyacyloxyalkyl esters (such as methylcarbonyloxymethyl, ethoxycarbonyloxyethyl and isopropoxycarbonyloxyethyl esters), alkoxyalkyl esters, choline esters and alkyl acylamino alkyl esters (such as acetamidomethyl esters).

A "solvate" is a complex formed by the combination of a solute (e.g., a metalloprotease inhibitor) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

The terms "optical isomer", "stereoisomer", and "diastereomer" have the standard art recognized meanings (see, e.g., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

II. Compounds

The subject invention involves compounds having a structure according to Formula (I)

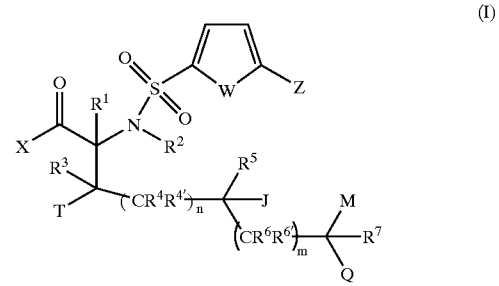

wherein
(A) X is selected from —OH and —NHOH; or when J is —D—$(CR^{14}R^{14'})$, $R^{15}$ where is D is —O—, as defined below, X can optionally be a covalent bond which joins with J to form a 5 to 9 membered ring; (preferably X is —OH)

(B) W is selected from —S—, —O—, —N($R^{32}$)—, —C($R^{32}$)=C($R^{32'}$)—, —N=C($R^{32}$)—, and —N=N— (preferably —S— or —C($R^{32}$)=C ($R^{32'}$)—), where $R^{32}$ and $R^{32'}$ each is independently selected from hydrogen, alkyl, alkenyl, alkynyl, heteroalkyl, aryl, heteroaryl, cycloalkyl, and heterocycloalkyl (preferably hydrogen);

(C) $R^1$ is selected from hydrogen, hydroxyl, alkoxy, alkyl, alkenyl, alkynyl, heteroalkyl, haloalkyl, cycloalkyl, heterocycloalkyl, aryl, arylalkyl, heteroaryl, heteroarylalkyl, and halogen (preferably hydrogen or alkyl, more preferably hydrogen);

(D) $R^2$ is selected from hydrogen, alkyl, alkenyl, alkynyl, heteroalkyl, haloalkyl, aryl, arylalkyl, heteroaryl, heteroarylalkyl, cycloalkyl, and heterocycloalkyl (preferably hydrogen or alkyl, more preferably hydrogen);

(E) T is —$(CR^8R^{8'})_p$—A—$(CR^{8''}R^{8'''})_q R^9$ where
  (1) p is from 0 to about 4 (preferably 0 or 1);
  (2) q is from 0 to about 4 (preferably 0 or 1);
  (3) each $R^8$, $R^{8'}$, $R^{8''}$, and $R^{8'''}$ is independently selected from hydrogen, alkyl, alkenyl, alkynyl, aryl, heteroalkyl, heteroaryl, cycloalkyl, heterocycloalkyl, halogen, and haloalkyl (preferably hydrogen);
  (4) $R^9$ is selected from hydrogen, alkyl, alkenyl, alkynyl, heteroalkyl, haloalkyl, cycloalkyl, heterocycloalkyl, aryl, heteroaryl, and halogen (preferably hydrogen, lower alkyl or aryl); and
  (5) A is selected from a covalent bond; —O—; —$SO_r$—, where r is 0, 1 or 2 (preferably 0 or 2); and —$NR^{10}$— where $R^{10}$ is selected from hydrogen, alkyl, alkenyl, alkynyl, heteroalkyl, aryl, heteroaryl, cycloalkyl, and heterocycloalkyl (preferably lower alkyl), or $R^{10}$ can join with $R^9$ to form a ring with 5 to 8 members (preferably 5 or 6) and 1 to 3 heteroatoms (preferably 1or 2); provided that when p is 0, A is a covalent bond;

(F) $R^3$ is selected from hydrogen, alkyl, alkenyl, alkynyl, aryl, heteroalkyl, heteroaryl, cycloalkyl, heterocycloalkyl, halogen, and haloalkyl (preferably hydrogen or lower alkyl);

(G) each $R^4$ and $R^{4'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy (preferably hydrogen); and n is from 0 to about 4 (preferably 0 or 1, more preferably 0);

(H) $R^5$ is —$(CR^{11}R^{11'})_sR^{12}$ where
  (1) s is from 0 to about 4 (preferably 0 or 1);
  (2) each $R^{11}$ and $R^{11'}$ is independently selected from hydrogen, alkyl, alkenyl, alkynyl, aryl, heteroalkyl, heteroaryl, cycloalkyl, heterocycloalkyl, halogen, and haloalkyl (preferably hydrogen); and
  (3) $R^{12}$ is selected from hydrogen, alkyl, alkenyl, alkynyl, heteroalkyl, haloalkyl, cycloalkyl, heterocycloalkyl, aryl, heteroaryl, halogen, and $GR^{13}$ where G is —O— or —S— and R is selected from hydrogen, alkyl, and aryl;

(I) J is —D—$(CR^{14}R^{14'})_tR^{15}$ where
  (1) t is from 0 to about 4 (preferably 0 or 1);
  (2) D is selected from —O—; —$SO_u$— where u is from 0 to 2 (preferably 0 or 2); and —$NR^{16}$— where $R^{16}$ is selected from hydrogen, alkyl, alkenyl, alkynyl, heteroalkyl, aryl, heteroaryl, cycloalkyl, and heterocycloalkyl (preferably lower alkyl), or $R^{16}$ can join with $R^{15}$ to form a ring with 5 to 8 members (preferably 5 or 6) and 1 to 3 heteroatoms (preferably 1 or 2);
  (3) each $R^{14}$ and $R^{14'}$ is independently selected from hydrogen, alkyl, alkenyl, alkynyl, aryl, heteroalkyl, heteroaryl, cycloalkyl, heterocycloalkyl, halogen, and haloalkyl (preferably hydrogen); and
  (4) $R^{15}$ is selected from hydrogen, alkyl, alkenyl, alkynyl, heteroalkyl, haloalkyl, cycloalkyl, heterocycloalkyl, aryl, and heteroaryl (preferably hydrogen, lower alkyl, aryl, and heteroaryl); or $R^{15}$ can join with $R^{13}$ to form an optionally substituted ring with 5 to 9 members of from 2 to 3 are heteroatoms;

(J) each $R^6$ and $R^{6'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy (preferably hydrogen); and m is from 0 to about 4 (preferably 0 or 1, more preferably 0);

(K) $R^7$ is —$(CR^{17}R^{17'})_vR^{18}$ where
  (1) v is from 0 to about 4 (preferably 0 or 1 );
  (2) $R^{17}$ and $R^{17'}$ are independently selected from hydrogen, alkyl, alkenyl, alkynyl, aryl, heteroalkyl, heteroaryl, cycloalkyl, heterocycloalkyl, halogen, and haloalkyl (preferably hydrogen); and
  (3) $R^{18}$ is selected from hydrogen, alkyl, alkenyl, alkynyl, heteroalkyl, haloalkyl, cycloalkyl, heterocycloalkyl, aryl, heteroaryl, and halogen (preferably hydrogen or lower alkyl);

(L) M is —E—$(CR^{19}R^{19'})_wR^{20}$ where
  (1) w is from 0 to about 4 (preferably 0 or 1);
  (2) E is selected from a —O—; —$SO_x$— where x is from 0 to 2 (preferably 0 or 2); and —$NR^{21}$— where $R^{21}$ is selected from hydrogen, alkyl, alkenyl, alkynyl, heteroalkyl, aryl, heteroaryl, cycloalkyl, and heterocycloalkyl (preferably lower alkyl), or $R^{21}$ can join with $R^{20}$ to form a ring with 5 to 8 members (preferably 5 or 6) and 1 to 3 heteroatoms (preferably 1 or 2);
  (3) each $R^{19}$ and $R^{19'}$ is independently selected from hydrogen, alkyl, alkenyl, alkynyl, aryl, heteroalkyl, heteroaryl, cycloalkyl, heterocycloalkyl, halogen, and haloalkyl (preferably hydrogen); and
  (4) $R^{20}$ is selected from hydrogen, alkyl, alkenyl, alkynyl, heteroalkyl, haloalkyl, cycloalkyl, heterocycloalkyl, aryl, and heteroaryl (preferably lower alkyl, aryl or heteroaryl);

(M) Q is —G'—$(CR^{22}R^{22'})_yR^{23}$ where
  (1) y is from 0 to about 4 (preferably 0 or 1)
  (2) G' is selected from a covalent bond; —O—; —$SO_z$— where z is from 0 to 2 (preferably 0 or 2); and —$NR^{24}$— where $R^{24}$ is selected from hydrogen, alkyl, alkenyl, alkynyl, heteroalkyl, aryl, heteroaryl, cycloalkyl, and heterocycloalkyl (preferably lower alkyl), or $R^{24}$ can join with $R^{22}$ to form a ring with 5 to 8 members (preferably 5 or 6) and 1 to 3 heteroatoms (preferably 1 or 2);
  (3) each $R^{22}$ and $R^{22'}$ is independently selected from hydrogen, alkyl, alkenyl, alkynyl, aryl, heteroalkyl, heteroaryl, cycloalkyl, heterocycloalkyl, halogen, and haloalkyl (preferably hydrogen); and
  (4) $R^{23}$ is selected from hydrogen, alkyl, alkenyl, alkynyl, heteroalkyl, haloalkyl, cycloalkyl, heterocycloalkyl, aryl, and heteroaryl (preferably hydrogen, lower alkyl, aryl or heteroaryl), or $R^{23}$ can join with $R^{20}$ to form a ring having from 5 to 8 members (preferably 5 or 6) with 1 to 3 heteroatoms (preferably 1 or 2); and (N) Z is selected from
  (1) cycloalkyl and heterocycloalkyl;
  (2) —D'—$(CR^{25}R^{25'})_aR^{26}$ where
    (a) a is from 0 to about 4 (preferably 0 or 1);
    (b) when a is from 0 to about 4 then D' is selected from —C≡C—, —CH=CH—, —O—, and —S—, and when a is from 1 to about 4, then D is selected from —C≡C—, —CH=CH—, —N=N—, —O—, —S— and —$SO_2$— (preferably —C≡C—, —CH=CH—, —O— or —S—);
    (c) each $R^{25}$ and $R^{25'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy (preferably hydrogen or lower alkyl); and (d) $R^{26}$ is selected from hydrogen, aryl, heteroaryl, alkyl, alkenyl, alkynyl, heteroalkyl, haloalkyl, heterocycloalkyl and cycloalkyl (preferably aryl, heteroaryl, heterocycloalkyl or cycloalkyl); and, if D' is —C≡C— or —CH=CH—, then $R^{26}$ may also be selected from —CONR$^{27}$R$^{27'}$ where (i) $R^{27}$ and $R^{27'}$ are independently selected from hydrogen, alkyl, alkenyl, alkynyl, haloalkyl, heteroalkyl, aryl, heteroaryl, cycloalkyl, and heterocycloalkyl, or (ii) $R^{27}$ and $R^{27'}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms;

(3) —NR$^{28}$R$^{28'}$ where (a) $R^{28}$ and $R^{28'}$ each is independently selected from hydrogen, alkyl, alkenyl, alkynyl, heteroalkyl, haloalkyl, aryl, heteroaryl, cycloalkyl, heteroalkyl (preferably hydrogen, alkyl or aryl) and —C(O)—Q'—(CR$^{29}$R$^{29'}$)$_b$R$^{30}$ where (i) b is from 0 to about 4 (preferably 0 or 1);

(ii) Q' is selected from a covalent bond and —NR$^{31}$— (preferably a covalent bond); and (iii) each $R^{29}$ and $R^{29'}$ is independently selected from hydrogen, alkyl alkenyl, alkynyl, aryl, heteroalkyl, heteroaryl, cycloalkyl, heterocycloalkyl, halogen, haloalkyl, hydroxy, and alkoxy (preferably hydrogen or lower alkyl, $R^{30}$ and $R^{31}$ (i) each is independently selected from hydrogen, alkyl, alkenyl, alkynyl, heteroalkyl, haloalkyl, aryl, heteroaryl, cycloalkyl, and heterocycloalkyl, or (ii) $R^{30}$ and $R^{31}$, together with the atoms to which they are bonded, join to form an optionally substituted heterocyclic ring containing from 5 to 8 (preferably 5 or 6) ring atoms of which from 1 to 3 (preferably 1 or 2) are heteroatoms (preferably $R^{30}$ is alkyl, aryl, heteroaryl, cycloalkyl or heterocycloalkyl); or $R^{28}$ and $R^{31}$, together with the nitrogen atoms to which they are bonded, join to form an optionally substituted heterocyclic ring containing from 5 to 8 ring atoms of which from 2 to 3 are heteroatoms; or (b) $R^{28}$ and $R^{28'}$, together with the nitrogen atom to which they are bonded, join to form an optionally substituted heterocyclic ring containing from 5 to 8 (preferably 5 or 6) ring atoms of which from 1 to 3 (preferably 1 or 2) are heteroatoms; and (4)

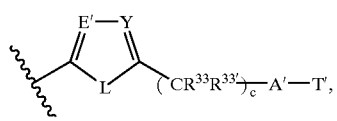

(4) where (a) E' and Y are independently selected from —CH— and —N—;

(b) L is selected from —S—, —O—, —N(R$^{35}$)—, —C(R$^{35}$)=C(R$^{35'}$)—, —N=C(R$^{35}$)—, and —N=N— [preferably —N=C(R$^{35}$)—or —C(R$^{35}$)=C(R$^{35'}$)—], where $R^{35}$ and $R^{35'}$ each is independently selected from hydrogen, alkyl, alkenyl, alkynyl, heteroalkyl, aryl, heteroaryl, cycloalkyl, and heterocycloalkyl (preferably hydrogen or lower alkyl);

(c) c is from 0 to about 4 (preferably 0 or 1);

(d) each $R^{33}$ and $R^{33'}$ is independently selected from hydrogen, alkyl, alkenyl, alkynyl, aryl, heteroalkyl, heteroaryl, cycloalkyl, heterocycloalkyl, halogen, haloalkyl, hydroxy, and alkoxy (preferably hydrogen or lower alkyl);

(e) A' is selected from a covalent bond, —O—, —SO$_d$—, —C(O)—, —C(O)NR$^{36}$—, —NR$^{36}$—, and —NR$^{36}$C(O)— [preferably —O—, —S—, SO$_2$—, —C(O)NR$^{36}$—, —NR$^{36}$—, and —NR$^{36}$C(O)—; more preferably —O—]; where d is from 0 to 2 and $R^{36}$ is selected from hydrogen, alkyl, alkenyl, alkynyl, aryl, heteroaryl, heteroalkyl, heteroaryl, cycloalkyl, heterocycloalkyl, haloalkyl (preferably lower alkyl or aryl); and (f) T' is —(CR$^{37}$R$^{37'}$)$_e$—R$^{38}$ where e is from 0 to about 4 (preferably 0or 1); each $R^{37}$ and $R^{37'}$ is independently selected from hydrogen, alkyl, alkenyl, alkynyl, aryl, heteroalkyl, heteroaryl, cycloalkyl, heterocycloalkyl, halogen, haloalkyl, hydroxy, alkoxy and aryloxy (preferably hydrogen or lower alkyl); and $R^{38}$ is selected from hydrogen, alkyl, alkenyl, alkynyl, halogen, heteroalkyl, haloalkyl, aryl, heteroaryl, cycloalkyl, and heterocycloalkyl (preferably lower alkyl or aryl); or $R^{36}$ and $R^{38}$, together with the atoms to which they are bonded, join to form an optionally substituted heterocyclic ring containing from 5 to 8 (preferably 5 or 6) atoms of which 1 to 3 (preferably 1 or 2) are heteroatoms; or $R^{35}$ and $R^{38}$, together with the atoms to which they are bonded, join to form an optionally substituted heterocyclic ring containing from 5 to 8 (preferably 5 or 6) atoms of which 1 to 3 (preferably 1 or 2) are heteroatoms;

or an optical isomer, diastereomer or enantiomer for Formula (I), or a pharmaceutically-acceptable salt, or biohydrolyzable amide, ester, or imide thereof.

III. Compound Preparation

The compounds of the invention can be prepared using a variety of procedures.

The starting materials used in preparing the compounds of the invention are known, made by known methods, or are commercially available. Particularly preferred syntheses are described in the following general reaction schemes. (The R groups used to illustrate the reaction schemes do not necessarily correlate to the respective R groups used to describe the various aspects of the Formula I compounds. That is, for example, $R^1$ in Formula (I) does not represent the same moiety as $R_1$ here.) Specific examples for making the compounds of the present invention are set forth in Section VIII, below.

Scheme 1

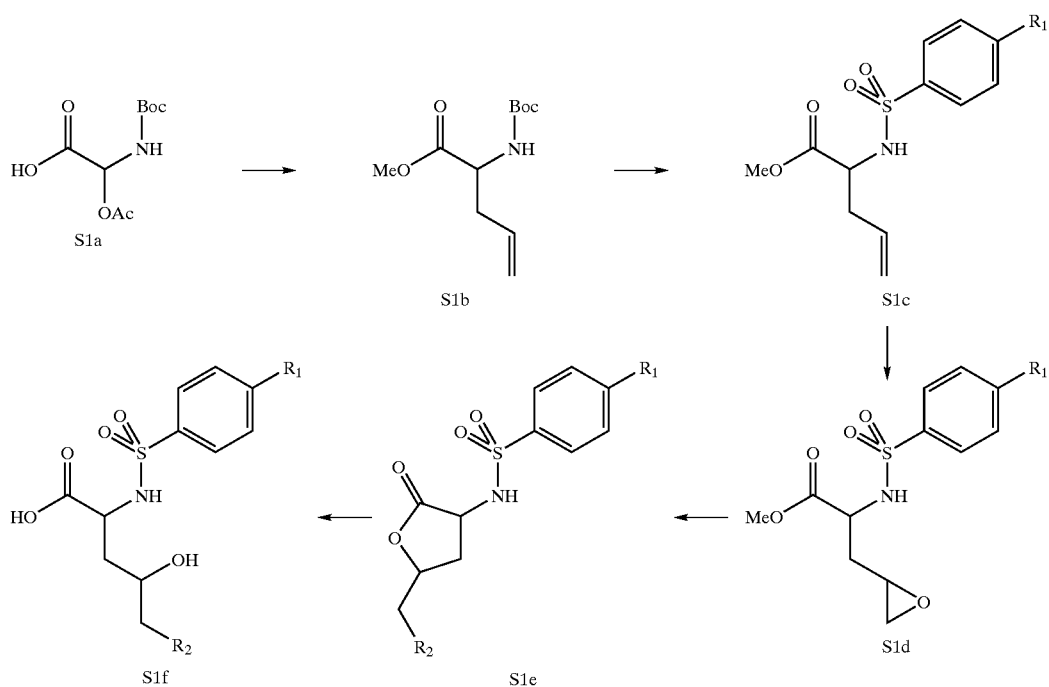

In Scheme 1, the acetate S1a depicted as starting material can be prepared from commercially available sources and converted to the corresponding allyl derivative such as S1b as described in *Tetrahedron Lett.* 1994, 35 (22), 3669.

Further functionalization of the alkene can be accomplished using methods well known to the skilled artisan. Such a process can be used to access a wide range of functionalities including but not limited to the epoxide S1d depicted in Scheme 1. Some form of nucleophilic addition to the epoxide ring can then occur, using well known methodology to produce the lactone S1e.

If desired, the ester functionality in compounds of type S1e can be transesterified, saponified to an acid or treated with basic hydroxyl amine to give the hydroxamic acid.

Scheme 2

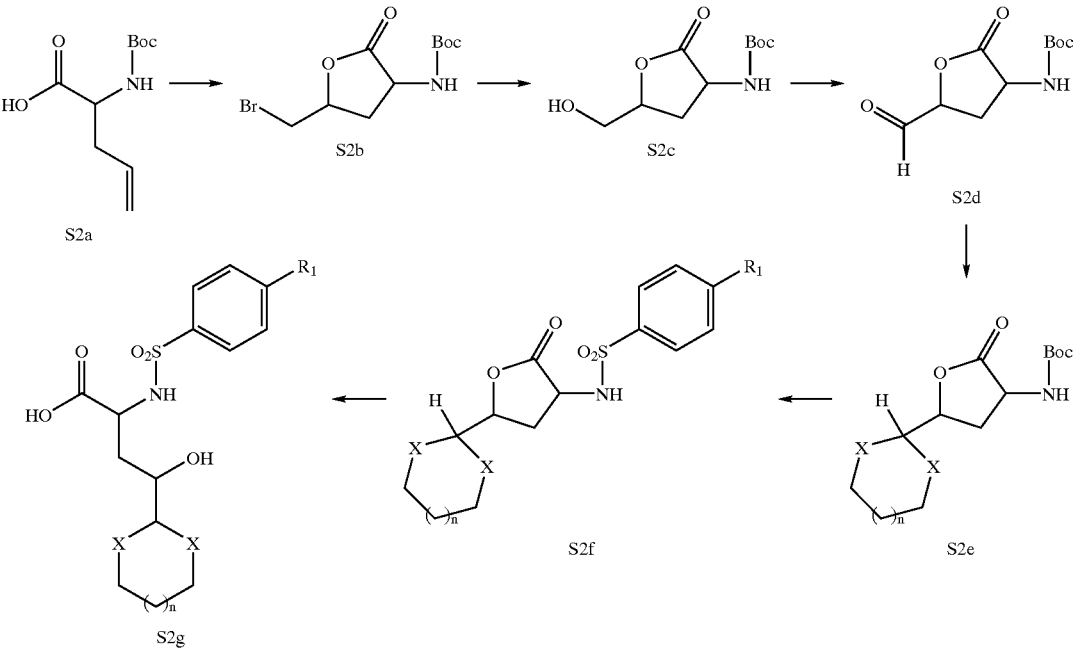

In Scheme 2, the allyl glycine S2a is converted to the aldehyde S2d using known methodology (Kurokawa et al, *Tetrahedron*, 1993, 49, 6195.). The aldehyde can then be transformed using known protecting group methods to the corresponding acetal, animal, or thioacetal S2e. The amine protecting group can then be removed and the sulfonamide group can be added. The lactone can then be transformed to the desired carboxylic acid S2g.

asymmetric way (Myers et al, *J. Am. Chem. Soc.* 1997, 119, 656.). These can then be functionalized according to known methods and carried forward as described above to generate a variety of compounds which fall within the scope of this invention.

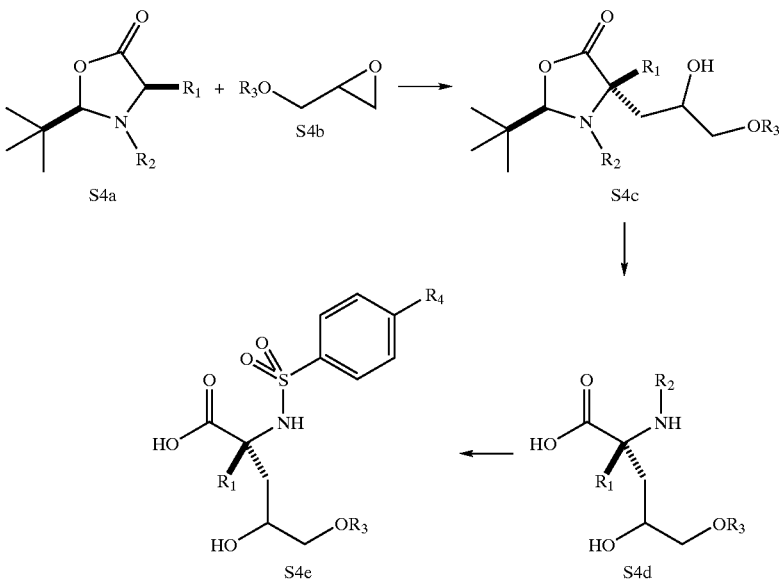

Scheme 4

The oxazolidinone S4a can be transformed to the aluminum enolate which can then react with the corresponding epoxide S4b to produce the alcohol S4c using known methodology (Smith et al, *J. Am. Chem. Soc.* 1995, 117, 11113.). The alcohol S4c can then be further elaborated to amino acid S4d using well described techniques. Final elaboration of the compound to produce S4e can occur in a manner analogous to that described above in Scheme 1.

A variety of compounds can be generated in a similar fashion, using the guidance of the schemes above.

It is recognized that it is preferable to use a protecting group for any reactive functionality such as a carboxyl, hydroxyl and the like, during the formation of the sultamester. This is standard practice, well within the normal practice of the skilled artisan.

In the above scheme, where R is alkoxy or alkylthio, the corresponding hydroxy or thiol compounds are derived from the final compounds by using a standard dealkylating procedure (Bhatt, et al., "Cleavage of Ethers", *Synthesis*, 1983, pp. 249–281).

These steps may be varied to increase yield of desired product. The skilled artisan will recognize the judicious choice of reactants, solvents, and temperatures is an important component in any successful synthesis. Determination of optimal conditions, etc. is routine. Thus the skilled artisan can make a variety of compounds using the guidance of the schemes above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and

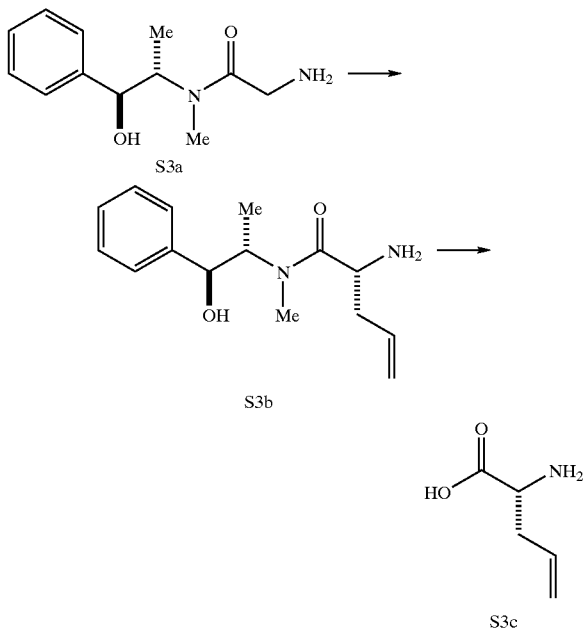

Scheme 3

Nucleophilic additions of the anion generated from amino acid condensate S3a to various electrophiles are a well known method for generating amino acids of type S3c in an nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will also readily appreciate that certain reactions are best carried out when another potentially reactive functionality on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantionmers, or stereoisomers substantially free of the other are disclosed and claimed as well.

IV. Methods of Use

Metalloproteases (MPs) found in the body operate, in part, by breaking down the extracellular matrix, which comprises extracellular proteins and glycoproteins. Inhibitors of metalloproteases are useful in treating diseases caused, at least in part, by the breakdown of such proteins and glycoproteins. These proteins and glycoproteins play an important role in maintaining the size, shape, structure and stability of tissue in the body. Thus, MPs are intimately involved in tissue remodeling.

As a result of this activity, MPs have been said to be active in many disorders involving either the: (1) breakdown of tissues including opthalmic diseases; degenerative diseases, such as arthritis, multiple sclerosis and the like; and metastasis or mobility of tissues in the body; or (2) remodeling of tissues including cardiac disease, fibrotic disease, scarring, benign hyperplasia, and the like.

The compounds of the present invention prevent or treat disorders, diseases and/or unwanted conditions which are characterized by unwanted or elevated activity by MPs. For example, the compounds can be used to inhibit MPs which:

1. destroy structural proteins (i.e. the proteins that maintain tissue stability and structure);
2. interfere in inter/intracellular signaling, including those implicated in cytokine up-regulation, and/or cytokine processing and/or inflammation, tissue degradation and other maladies [Mohler K M, et al, Nature 370 (1994) 218–220, Gearing A J H, et al, Nature 370 (1994) 555–557 McGeehan G M, et al, Nature 370 (1994) 558–561]; and
3. facilitate processes which are undesired in the subject being treated, for example, the processes of sperm maturation, egg fertilization and the like.

As used herein, an "MP related disorder" or "MP related disease" is one that involves unwanted or elevated MP activity in the biological manifestation of the disease or disorder; in the biological cascade leading to the disorder; or as a symptom of the disorder. This "involvement" of the MP includes:

1. The unwanted or elevated MP activity as a "cause" of the disorder or biological manifestation, whether the activity is elevated genetically, by infection, by autoimmunity, trauma, biomechanical causes, lifestyle [e.g. obesity] or by some other cause;
2. The MP as part of the observable manifestation of the disease or disorder. That is, the disease or disorder is measurable in terms of the increased MP activity. From a clinical standpoint, unwanted or elevated MP levels indicate the disease, however, MPs need not be the "hallmark" of the disease or disorder; or
3. The unwanted or elevated MP activity is part of the biochemical or cellular cascade that results or relates to the disease or disorder. In this respect, inhibition of the MP activity interrupts the cascade, and thus controls the disease.

The term "treatment" is used herein to mean that, at a minimum, administration of a compound of the present invention mitigates a disease associated with unwanted or elevated MP activity in a mammalian subject, preferably in humans. Thus, the term "treatment" includes: preventing an MP-mediated disease from occurring in a mammal, particularly when the mammal is predisposed to acquiring the disease, but has not yet been diagnosed with the disease; inhibiting the MP-mediated disease; and/or alleviating or reversing the MP-mediated disease. Insofar as the methods of the present invention are directed to preventing disease states associated with unwanted MP activity, it is understood that the term "prevent" does not require that the disease state be completely thwarted. (See Webster's Ninth Collegiate Dictionary.) Rather, as used herein, the term preventing refers to the ability of the skilled artisan to identify a population that is susceptible to MP-related disorders, such that administration of the compounds of the present invention may occur prior to onset of the disease. The term does not imply that the disease state be completely avoided. For example, osteoarthritis (OA) is the most common rhueumatological disease with some joint changes radiologically detectable in 80% of people over 55 years of age. Fife, R. S., "A Short History of Osteoarthritis", Osteoarthritis: Diagnosis and Medical/Surgical Management, R. W. Moskowitz, D. S. Howell, V. M. Goldberg and H. J. Mankin Eds., p 11–14 (1992). A common risk factor that increases the incidence of OA is traumatic injury of the joint. Surgical removal of the meniscus following knee injury increases the risk of radiographically detectable OA and this risk increases with time. Roos, H et al. "Knee Osteoarthritis After Menisectomy: Prevalence of Radiographic Changes After Twenty-one Years, Compared with Matched Controls." Arthritis Rheum., Vol. 41, pp 687–693; Roos, H et al. "Osteoarthritis of the Knee After Injury to the Anterior Cruciate Ligament or Meniscus: The Influence of Time and Age." Osteoarthritis Cartilege., Vol. 3, pp 261–267 (1995). Thus, this patient population is identifiable and could receive administration of a compound of the present invention before progression ef the disease. Thus, progression of OA in such individuals would be "prevented".

Advantageously, many MPs are not distributed evenly throughout the body. Thus, the distribution of MPs expressed in various tissues are often specific to those tissues. For example, the distribution of metalloproteases implicated in the breakdown of tissues in the joints is not the same as the distribution of metalloproteases found in other tissues. Though not essential for activity or efficacy, certain diseases, disorders, and unwanted conditions preferably are treated with compounds that act on specific MPs found in the affected tissues or regions of the body. For example, a compound which displays a higher degree of affinity and inhibition for an MP found in the joints (e.g. chondrocytes) would be preferred for treatment of a disease, disorder, or unwanted condition found there than other compounds which are less specific.

In addition, certain inhibitors are more bioavailable to certain tissues than others. Choosing an MP inhibitor which is more bioavailable to a certain tissue and which acts on the specific MPs found in that tissue, provides for specific treatment of the disease, disorder, or unwanted condition. For example, compounds of this invention vary in their ability to penetrate into the central nervous system. Thus, compounds may be selected to produce effects mediated through MPs found specifically outside the central nervous system.

Determination of the specificity of an inhibitor of a specific MP is within the skill of the artisan in that field. Appropriate assay conditions can be found in the literature. Specifically, assays are known for stromelysin and collagenase. For example, U.S. Pat. No. 4,743,587 references the procedure of Cawston, et al., *Anal Biochem* (1979) 99:340–345. See also, Knight, C. G. et al., "A Novel Coumarin-Labelled Peptide for Sensitive Continuous Assays of the Matrix Metalloproteases", *FEBS Letters,* Vol. 296, pp. 263–266 (1992). The use of a synthetic substrate in an assay is described by Weingarten, H., et al., *Biochem Biophy Res Comm* (1984) 139:1184–1187. Any standard method for analyzing the breakdown of structural proteins by MPs can, of course, be used. The ability of compounds of the invention to inhibit metalloprotease activity can, of course, be tested in the assays found in the literature, or variations thereof. Isolated metalloprotease enzymes can be used to confirm the inhibiting activity of the invention compounds, or crude extracts which contain the range of enzymes capable of tissue breakdown can be used.

The compounds of this invention are also useful for prophylactic or acute treatment. They are administered in any way the skilled artisan in the fields of medicine or pharmacology would desire. It is immediately apparent to the skilled artisan that preferred routes of administration will depend upon the disease state being treated and the dosage form chosen. Preferred routes for systemic administration include administration perorally or parenterally.

However, the skilled artisan will readily appreciate the advantage of administering the MP inhibitor directly to the affected area for many diseases, disorders, or unwanted conditions. For example, it may be advantageous to administer MP inhibitors directly to the area of the disease, disorder, or unwanted condition such as in the area affected by surgical trauma (e. g., angioplasty), scarring, burning (e.g., topical to the skin), or for opthalmic and periodontal indications.

Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in, joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure over time) is that MP activity is not desired or is elevated in response to what may be recognized by the body as "injury" to the basement membrane of the vessel. Thus regulation of MP activity in indications such as dilated cardiomyopathy, congestive heart failure, atherosclerosis, plaque rupture, reperfusion injury, ischemia, chronic obstructive pulmonary disease, angioplasty restenosis and aortic aneurysm may increase long term success of any other treatment, or may be a treatment in itself.

In skin care, MPs are implicated in the remodeling or "turnover" of skin. As a result, the regulation of MPs improves treatment of skin conditions including but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultraviolet damage and/or during or after exposure to prevent or minimize post-exposure damage. In addition, MPs are implicated in skin disorders and diseases related to abnormal tissues that result from abnormal turnover, which includes metalloprotease activity, such as epidermolysis bullosa, psoriasis, scleroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly in diseases such as multiple sclerosis, MPs may be involved in the irregular modeling of blood brain barrier and/or myelin sheaths of nervous tissue. Thus regulating MP activity may be used as a strategy in treating, preventing, and controlling such diseases.

MPs are also thought to be involved in many infections, including cytomegalovirus [CMV]; retinitis; HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

In addition they are also contemplated to be useful in preventing or stopping premature labor and delivery.

Since MPs are implicated in the inflammatory response and in the processing of cytokines, the compounds are also useful as anti-inflammatories, for use in disease where inflammation is prevalent including, inflammatory bowel disease, Crohn's disease, ulcerative colitis, pancreatitis, diverticulitis, asthma or related lung disease, rheumatoid arthritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including, lupus erythmatosis, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis, acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives. For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and perhaps regulation of hair growth.

For some diseases, conditions or disorders MP inhibition is contemplated to be a preferred method of treatment. Such diseases, conditions or disorders include, arthritis (including osteoarthritis and rheumatoid arthritis), cancer (especially the prevention or arrest of tumor growth and metastasis), ocular disorders (especially corneal ulceration, lack of corneal healing, macular degeneration, and pterygium), and gum disease (especially periodontal disease, and gingivitis)

Compounds preferred for, but not limited to, the treatment of arthritis (including osteoarthritis and rheumatoid arthritis) are those compounds that are selective for the matrix metalloproteases and the disintegrin metalloproteases.

Compounds preferred for, but not limited to, the treatment of cancer (especially the prevention or arrest of tumor growth and metastasis) are those compounds that preferentially inhibit gelatinases or type IV collagenases.

Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel.

Compounds preferred for, but not limited to, the treatment of gum disease (especially periodontal disease, and gingivitis) are those compounds that preferentially inhibit collagenases.

V. Compositions

The compositions of the invention comprise:
(a) a safe and effective amount of a compound of the invention; and
(b) a pharmaceutically-acceptable carrier.

As discussed above, numerous diseases are known to be mediated by excess or undesired metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences,* Mack Publishing Company, Easton, Pa., latest edition.

A "safe and effective amount" of a Formula (I) compound is an amount that is effective, to inhibit metalloproteases at the site(s) of activity, in an animal, preferably a mammal, more preferably a human subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics,* Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents. flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents. such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve low characteristics of the powder mixture. Coloring agents, suh as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel" RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit" coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a sat an effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emolients, emulsifiers, thickening agents, solvents and the like.

VI. Methods of Administration

This invention also provides methods of treating or preventing disorders associated with excess or undesired metalloprotease activity in a human or other animal subject, by administering a safe and effective amount of a Formula (I) compound to said subject. As used herein, a "disorder associated with excess or undesired metalloprotease activity" is any disorder characterized by degradation of matrix proteins. The methods of the invention are useful in treating or preventing disorders described above.

Compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the metalloprotease is accumulated by using targeting ligands. For example, to focus the inhibitors to metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. For treatment of oral diseases, the compound may be applied locally in a gel, paste, mouth wash, or implant. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases. Some bacterial metalloproteases may be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

VII. Preparation and Use of Antibodies

Metalloproteases active at a particularly undesired location (e.g., an organ or certain types of cells) can be targeted by conjugating the compounds of the invention to a targeting ligand specific for a marker at that location such as an antibody or fragment thereof or a receptor ligand. Conjugation methods are known in the art.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired metalloprotease.

In another aspect, the invention is directed to the compounds of Formula (I) conjugated to label. As the compounds of the invention bind to at least one metalloprotease, the label can be used to detect the presence of relatively high levels of metalloprotease in vivo or in vitro cell culture.

In addition, the compounds of Formula (I) can be conjugated to carriers which permit the use of these compounds in immunization protocols to prepare antibodies specifically immunoreactive with the compounds of the invention. Typical conjugation methods are known in the art. These antibodies are then useful both in therapy and in monitoring the dosage of the inhibitors.

The invention compounds can also be coupled to labels such as scintigraphic labels, e.g., technetium 99 or I-131, using standard coupling methods. The labeled compounds are administered to subjects to determine the locations of excess amounts of one or more metalloproteases in vivo. The ability of the inhibitors to selectively bind metalloprotease is thus taken advantage of to map the distribution of these enzymes in situ. The techniques can also be employed in histological procedures and the labeled invention compounds can be used in competitive immunoassays.

The following non-limiting examples illustrate the compounds, compositions, and uses of the present invention.

VIII. EXAMPLES—COMPOUND PREPARATION

The R groups used to illustrate the compound examples do not correlate to the respective R groups used to describe the various moieties of Formula (I). That is, for example, $R^1$, $R^2$ and $R^3$ used to describe Formula (I) in Section 11 of the Detailed Description do not represent the same moieties as $R_1$, $R_2$, and $R_3$ in this Section VIII.

Typically tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merck) as appropriate. Thin layer chromatography analysis (TLC) is performed on glass mounted silica gel plates (200–300 mesh; Baker) and visualized with UV or 5% phosphomolybdic acid in ethanol (EtOH).

The following abbreviations are used herein:

| | |
|---|---|
| MeOH: methanol | Et₃N: triethylamine |
| EtOAc: ethylacetate | Et₂O: diethylether |
| Ph: phenyl | boc: t-butyloxycarbonyl |
| DMF: N,N-dimethylformamide | acac: acetyl acetate |
| DME: dimethoxyethane | dil.: dilute |
| conc.: concentrated | wrt.: with respect to |

Examples 1–61

The following chemical formula along with Table 1 shows the structure of compounds made according to the description in Examples 1–61 described below.

TABLE 1

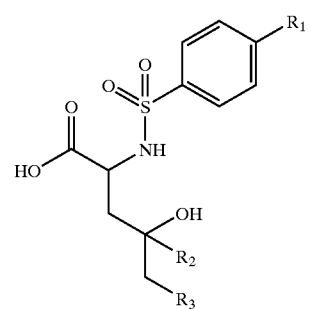

| Example | R₁ | R₂ | R₃ |
|---|---|---|---|
| 1 | —C₆H₄—OMe | —H | —S-thiazol-2-yl |
| 2 | —C₆H₄—SMe | —H | —S-thiazol-2-yl |
| 3 | —C₆H₄—OPh | —H | —S-thiazol-2-yl |
| 4 | —C₆H₄—O—CH₂CH₂—O—CH₃ | —H | —S-thiazol-2-yl |
| 5 | —C₆H₄—O—CH₂CH₂—N(pyrrolidine) | —H | —S-thiazol-2-yl |

TABLE 1-continued

| Example | R₁ | R₂ | R₃ |
|---|---|---|---|
| 6 | 4-biphenyl | —H | 2-thiazolylthio |
| 7 | benzo[1,3]dioxol-5-yl | —H | 2-thiazolylthio |
| 8 | 3-ethoxyphenyl | —H | 2-thiazolylthio |
| 9 | (4-methoxyphenyl)ethynyl | —H | 2-thiazolylthio |
| 10 | (4-methylphenyl)ethynyl | —H | 2-thiazolylthio |
| 11 | phenylazo | —H | 2-thiazolylthio |
| 12 | 4-chlorophenyl | —H | 2-thiazolylthio |

TABLE 1-continued

| Example | R₁ | R₂ | R₃ |
|---|---|---|---|
| 13 | 4-Br-phenyl | —H | 2-thiazolyl-S- |
| 14 | 4-CF₃-phenyl | —H | 2-thiazolyl-S- |
| 15 | 4-OMe-phenyl | —H | phenyl-S- |
| 16 | phenyl | —H | phenyl-S- |
| 17 | 4-OMe-phenyl | —H | benzyl-S- |
| 18 | 4-OMe-phenyl | —H | benzyl-SO₂- |
| 19 | 4-OMe-phenyl | —H | phenyl-NH- |
| 20 | 4-OMe-phenyl | —H | 1,2,4-triazol-3-yl-S- |

TABLE 1-continued

| Example | R₁ | R₂ | R₃ |
|---------|------|------|------|
| 21 | 4-MeO-C₆H₄- | —H | N(Me)(Ph) |
| 22 | 4-MeO-C₆H₄- | —H | S-(1H-imidazol-2-yl) |
| 23 | 4-MeO-C₆H₄- | —H | S-(5-methyl-1H-benzimidazol-2-yl) |
| 24 | 4-MeO-C₆H₄- | —H | S-(4-oxo-3H-quinazolin-2-yl) |
| 25 | 4-MeO-C₆H₄- | —H | S-(6-ethoxy-benzothiazol-2-yl) |
| 26 | 4-MeO-C₆H₄- | —H | S-(benzothiazol-2-yl) |
| 27 | 4-MeO-C₆H₄- | —H | S-(benzoxazol-2-yl) |
| 28 | 4-MeO-C₆H₄- | —H | S-(1H-benzimidazol-2-yl) |

TABLE 1-continued

| Example | R₁ | R₂ | R₃ |
|---------|----|----|----|
| 29 | 4-MeO-C₆H₄– | –H | 1-methylimidazol-2-ylthio |
| 30 | 4-MeO-C₆H₄– | –H | 1-methyltetrazol-5-ylthio |
| 31 | 4-MeO-C₆H₄– | –H | 5-methyl-1,3,4-thiadiazol-2-ylthio |
| 32 | 4-MeO-C₆H₄– | –H | 4-methyl-4H-1,2,4-triazol-3-ylthio |
| 33 | 4-MeO-C₆H₄– | –H | 5-(methylthio)-1,3,4-thiadiazol-2-ylthio |
| 34 | 4-MeO-C₆H₄– | –H | thien-2-ylthio |
| 35 | 4-MeO-C₆H₄– | –H | 5-phenyl-1,3,4-oxadiazol-2-ylthio |

TABLE 1-continued

| Example | R₁ | R₂ | R₃ |
|---|---|---|---|
| 36 | 4-MeO-C₆H₄- | —H | -S-(1-(4-methoxyphenyl)-1H-tetrazol-5-yl) |
| 37 | 4-MeO-C₆H₄- | —H | -S-(6-chlorobenzoxazol-2-yl) |
| 38 | 4-MeO-C₆H₄- | —H | -S-(3-methylthio-1,2,4-thiadiazol-5-yl) |
| 39 | 4-MeO-C₆H₄- | —H | -S-(5-(pyridin-4-yl)-1,3,4-oxadiazol-2-yl) |
| 40 | 4-MeO-C₆H₄- | —H | -S-(5-methoxybenzothiazol-2-yl) |
| 41 | 4-MeO-C₆H₄- | —H | -S-(5-methoxy-1H-benzimidazol-2-yl) |
| 42 | 4-MeO-C₆H₄- | —H | -S-(5-phenyl-1H-1,2,4-triazol-3-yl) |
| 43 | 4-MeO-C₆H₄- | —H | -S-(2-methylfuran-3-yl) |

TABLE 1-continued
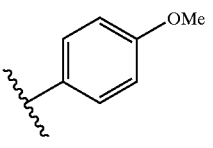
| Example | R₁ | R₂ | R₃ |
|---|---|---|---|
| 44 | 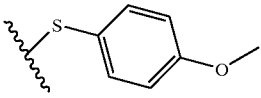 | —H | 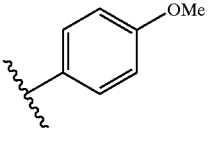 |
| 45 | 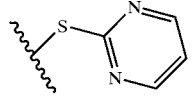 | —H | 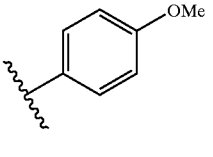 |
| 46 | 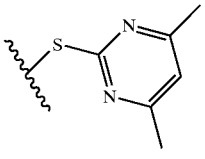 | —H | 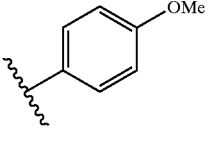 |
| 47 | 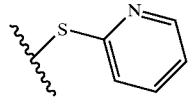 | —H | 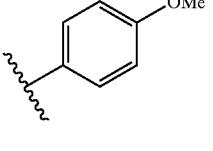 |
| 48 | 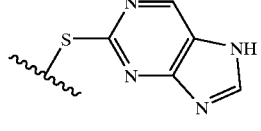 | —H | 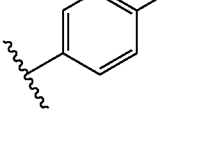 |
| 49 | 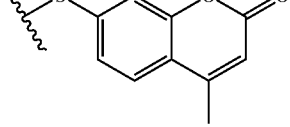 | —H | 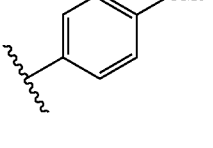 |
| 50 | 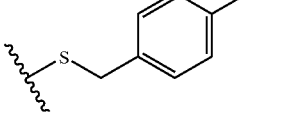 | —H | 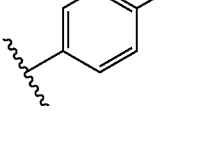 |
| 51 | 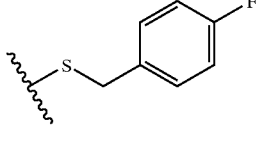 | —H |  |

TABLE 1-continued
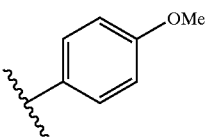
| Example | R₁ | R₂ | R₃ |
|---|---|---|---|
| 52 | 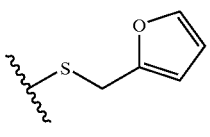 | —H | 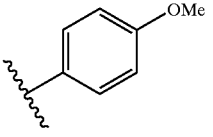 |
| 53 | 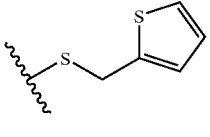 | —H | 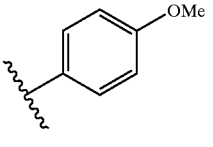 |
| 54 | 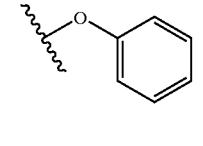 | —H | 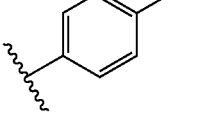 |
| 55 | 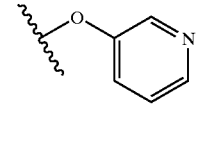 | —H | 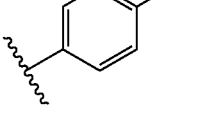 |
| 56 | 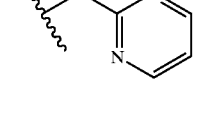 | —H | 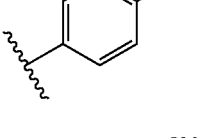 |
| 57 | 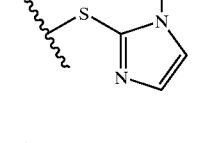 | —Me | 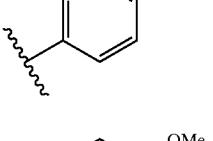 |
| 58 | 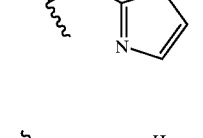 | —Me | 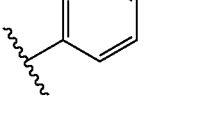 |
| 59 | 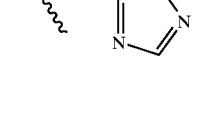 | —Me |  |

TABLE 1-continued

| Example | R₁ | R₂ | R₃ |
|---|---|---|---|
| 60 | 4-OMe-phenyl | —H | 2-(3-CF₃-pyridyl)thio |
| 61 | 4-OMe-phenyl | —Me | 2-(3-CF₃-pyridyl)thio |

Example 1

Preparation of 2-[(4'-Methoxy[1,1'-biphenyl]-4-yl)sulfonyl]amino-4-hydroxy-5-[(2-thiazolyl)thio]-pentanoic acid a. N-Boc-allylglycine methyl ester

To a mixture of acetyloxy[[(1,1-dimethylethoxy)carbonyl]amino]acetic acid methyl ester (Ref. Tetrahedron Lett. 1994, 35 3669, 21.1 g, 85.7 mmol), zinc (11.2 g, 171.42 mmol) and DMF (100 mL) at 0° C. is added allylbromide (14.8 mL, 171.4 mmol) dropwise. The reaction is warmed to room temperature and stirred overnight. The mixture is diluted with 0.1N HCl and hexane/EtOAc (2:1), filtered, the reaction mixture is then extracted three times with hexane/EtOAc (2:1). The combined EtOAc layer is washed twice with 0.1 N HCl, brine/H₂O, brine, dried over MgSO₄, and concentrated under reduced pressure to give an oil.

b. Methyl 2-[4-(iodophenyl)sulfonylamino]-pent-4-enoate

To a solution of N-Boc-allylglycine methyl ester 1a (19.6 g, 85.6 mmol) in CH₂Cl₂ (40 mL) at 0° C. is added trifluoroacetic acid (33 mL, 428 mmol) slowly, and the resulting mixture is stirred overnight at room temperature. The reaction mixture is concentrated under reduced pressure to dryness then dissolved in dioxane (50 mL) and water (30 mL). To the solution is added triethylamine (35.7 mL, 256.8 mmol), followed by 4-iodobenzenesulfonyl chloride (28.6 g, 89.9 mmol) and the mixture is stirred overnight. The reaction mixture is diluted with water, and extracted three times with EtOAc. The combined EtOAc layer is washed consecutively with 1 N HCl, H₂O, and then brine. The organic layers are dried, and concentrated to an oil which solidifies upon standing to give the desired product.

c. Methyl 2-[(4'-methoxy[1,1'-biphenyl]-4-yl)sulfonylamino]-pent-4-enoate

To a solution of methyl 2-[4-(iodophenyl)sulfonylamino]-pent-4-enoate 1b (35 g, 85.9 mmol) in benzene (400 mL), 2N NaHCO₃ (18 g, 171 mmol, in 65 mL of water) at room temperature is added slowly tetrakis(triphenylphosphine)palladium(0) (2.96 g, 2.5 mmol), followed by 4-methoxyphenylboronic acid (19.6 g, 128.4 mmol) in EtOH (40 mL). The reaction mixture is heated to reflux for 5.5 h. The solution is then cooled to room temperature, and H₂O₂ (4.4 mL, 43 mmol, 30% wt aqueous solution) is added to the reaction and the resulting mixture is stirred for 10 min and then diluted with water. The mixture is extracted three times with Et₂O. The combined Et₂O layer is washed with brine, dried over MgSO₄ and concentrated to a solid which is recrystallized from EtOAc/hexane to give the desired product.

d. Methyl 2-[(4'-methoxy[1,1'-biphenyl]-4-yl)sulfonyl]amino-4,5-epoxypentanoate To a solution of methyl 2-[(4'-methoxy[1,1'-biphenyl]-4-yl)sulfonylamino]-pent-4-enoate 1(15.3 g, 40.8 mmol) in CH₂Cl₂(150 mL), NaHCO₃ (7.1 g, 85 mmol) and water (80 mL) at 0° C., is added slowly m-chloroperbenzoic acid (32.6 g, ~123 mmol, 57–86%). The reaction mixture is stirred overnight. The reaction is then diluted with aqueous NaHCO₃ and the mixture is extracted three times with EtOAc. The combined EtOAc layer is washed with NaHCO₃, brine, dried over MgSO₄ and concentrated to an oil. Purification is accomplished by column chromatography with EtOAc/hexane (3:7 to 6:4) as the eluent to give the desired product as a mixture of two isomers (ratio 2:3).

e. 3-[(4'-Methoxy[1,1'-biphenyl]-4-yl)sulfonyl]amino-[2-oxo-5-(thiazol-2-yl)thio]methyl]-tetrahydrofuran To a solution of methyl 2-[(4'-methoxy[1,1'-biphenyl]-4-yl)sulfonyl]amino-4,5-epoxypentanoate 1d (0.7 g, 1.79 mmol) in benzene (5 mL) and Et₃N (0.33 mL, 2.3 mmol) at room temperature is added slowly 2-mercaptothiazole (0.52 g, 4.48 mmol). The reaction mixture is stirred for 4 h at room temperature. The resulting mixture is diluted with water, and the mixture is then extracted three times with EtOAc. The combined EtOAc layer is consecutively washed with water, and brine, dried over $MgSO_4$ and concentrated to an oil under reduced pressure. Purification is accomplished by column chromatography with hexane/EtOAc (4:1 to 7:3 to 6:4) eluent to give the desired product.

f. 2-[(4'-Methoxy[1,1'-biphenyl]-4-yl)sulfonyl] amino-4-hydroxy-5-[(2-thiazolyl)thio]-pentanoic acid To a solution of 3-[(4'-methoxy[1,1'-biphenyl]-4-yl) sulfonyl]amino-[2-oxo-5-(thiazol-2-yl)thio]methyl]-tetrahydrofuran 1e (0.38 g, 0.80 mmol) in water (5 mL) and THF (5 mL) is slowly added lithium hydroxide monohydrate (330 mg, 8 mmol). The reaction mixture is stirred for 2 h, then concentrated to dryness. The reaction is then diluted with water, and then the mixture is extracted twice with $Et_2O$. The $Et_2O$ layer is discarded and the aqueous layer is neutralized carefully with 1N HCl to pH 6, and then extracted three times with EtOAc. The combined EtOAc layer is washed with brine, dried over $MgSO_4$ and concentrated to a solid which is recrystallized from EtOAc/hexane to give the desired product as a white solid.

Example 2

2-[(4'-(Methylthio)[1,1'-biphenyl]-4-yl)sulfonyl] amino-4-hydroxy-5-[(2-thiazolyl)thio]-pentanoic acid Example 2 is prepared from 4-(methylthio)phenylboronic acid and 1c using the procedure described for compound 1.

Example 3

2-[(4'-Phenoxy[1,1'-biphenyl]-4-yl)sulfonyl]amino-4-hydroxy-5-[(2-thiazolyl) thio]-pentanoic acid Example 3 is prepared from 4-(phenoxy)phenylboronic acid and 1c using the procedure described for compound 1.

Example 4

2-[(4'-(2-Methoxyethoxy)[1,1'-biphenyl]-4-yl) sulfonyl]amino-4-hydroxy-5-](2-thiazolyl)thio]-pentanoic acid Example 4 is prepared from 4-(2-methoxyethoxy) phenylboronic acid and 1c using the procedure described for compound 1.

Example 5

2-[(4'-(2-(1-Pyrrolidinyl)ethoxy)[1,1'-biphenyl]-4-yl) sulfonyl]amino-4-hydroxy-5-[(2-thiazolyl)thio]-pentanoic acid Example 5 is prepared from 4-(2-(1-pyrrolidinyl)ethoxy) phenylboronic acid and 1c using the procedure described for compound 1.

Example 6

2-[(1,1':4',1''-Terphenyl]-4-yl)sulfonyl]amino-4-hydroxy-5-[(2-thiazolyl)thio]-pentanoic acid Example 6 is prepared from 4-biphenylboronic acid and 1c using the procedure described for compound 1.

Example 7

2-[(3', 4'-(Methylenedioxy)[1,1'-biphenyl]-4-yl) sulfonyl]amino-4-hydroxy-5-[(2-thiazolyl)thio]-pentanoic acid Example 7 is prepared from 4-methylenedioxyphenylboronic acid and 1c using the procedure described for compound 1.

Example 8

2-[(3'-Ethoxy[1,1'-biphenyl[-4-yl)sulfonyl]amino-4-hydroxy-5-[(2-thiazolyl)thio]-pentanoic acid Example 8 is prepared from 3-ethoxyphenylboronic acid and 1c using the procedure described for compound 1.

Example 9

2-[[4-[(4-Methoxyphenyl)ethynyl]phenyl]sulfonyl] amino-4-hydroxy-5-[(2-thiazolyl)thio]-pentanoic acid Example 9 is prepared from 1-ethynyl-4-methoxybenzene and 1c using the procedure described for compound 1.

Example 10

2-[[4-[(4-Methylphenyl)ethynyl]phenyl]sulfonyl] amino-4-hydroxy-5-[(2-thiazolyl)thio]-pentanoic acid Example 10 is prepared from 1-ethynyltoluene and 1c using the procedure described for compound 1.

Example 11

2-[[4-(Phenylazo)phenyl]sulfonyl]amino-4-hydroxy-5-[(2-thiazolyl)thio]-pentanoic acid Example 11 is prepared from 4-phenylazobenzene sulfonyl chloride and 1a using the procedure described for compound 1.

Example 12

2-[(4'-Chloro[1,1'-biphenyl]-4-yl)sulfonyl]amino-4-hydroxy-5-[2-thiazolylthio]-pentanoic acid a. 4'-Chlorobiphenyl-4-sulfonic acid To a solution of 4-chlorobiphenyl (15 g, 79.8 mmol) in chloroform (150 mL) is added dropwise chlorosulfonic acid (11.2 g, 96 mmol). A white solid precipitate forms during the addition. The reaction is stirred at room temperature for 6 hr, at which time the precipitate is collected by filtration and the precipitate is then washed with cold chloroform. The product is dried under vacuum to give a white solid product. The product is used without further purification.

b. 4'-Chlorobiphenyl-4-sulfonyl chloride

To a solution of 4'-chlorobiphenyl-4-sulfonic acid 12a (15.1 g ,78.1 mmol)in thionyl chloride (150 mL) is added a catalytic amount of N,N-dimethylformamide (0.3 mL). The reaction mixture is heated to reflux for 4 hr. The mixture is then cooled to room temperature, and concentrated under reduced pressure. Toluene is then added and the mixture is concentrated under reduced pressure. The solid crude product is then recrystallized with ethyl acetate and hexanes to give the solid desired product.

c. Methyl 2-[4'-(chloro[1',1'-biphenyl]-yl)-4-sulfonylamino]-pent-4-enoate

To a solution of allylglycine methyl ester hydrochloride (5 g, 30.2 mmol) in CH$_2$Cl$_2$ (150 mL) at 0 C. is added triethylamine (9.2 g, 90.6 mmol), followed by 4-chlorobiphenyl-4-sulfonyl chloride 12b (9.1 g, 31.7 mmol) and the mixture is allowed to warm to room temperature and is stirred overnight. The reaction mixture is diluted with water, extracted 3 times with ethyl acetate. The combined ethyl acetate layer is washed with 1 N HCl and brine. The organic layers are dried with MgSO$_4$, filtered, and concentrated to an oil which is allowed to stand and solidify to the desired product.

d. Methyl 2-[(4'-chloro[1,1'-biphenyl]-4-yl)-sulfonyl]amino-4,5-epoxypentanoate To a solution of methyl 2-[(4'-chloro[1,1'-biphenyl]-4-yl)-sulfonylamino]-pent-4-eneoate 12c (9.2 g, 24.1 mmol) in CH$_2$Cl$_2$ (175 mL), NaHCO$_3$ (4.2 g, 50 mmol) and water (100 mL) at 0 C., is slowly added m-chloroperbenzoic acid (57–86%) (19.4 g, ~80 mmol). The reaction is stirred for 72 hours. The mixture is diluted with aqueous NaHCO$_3$ and this mixture is extracted with ethyl acetate (3×100 mL). The combined ethyl acetate layer is washed with brine, dried over MgSO$_4$, filtered and concentrated to an oil. Purification of this compound is accomplished by column chromatography with 40% ethyl acetate in hexanes as the eluent to give the desired product.

e. 3-[(4'-Chloro[1,1'-biphenyl]-4-yl)sulfonyl]amino-[2-oxo-5-(thiazol-2-yl)thio]methyl]-tetrahydrofuran To a solution of methyl 2-[(4'-chloro[1,1'-biphenyl]-4-yl]amino-4,5-epoxypentanoate 12d (2.6 g, 6.5 mmol) in benzene (10 mL) and triethylamine (0.95 mL, 6.85 mmol) at room temperature is added slowly 2-mercaptothiazole (1.52 g, 13 mmol). The reaction is stirred overnight at room temperature. The resulting mixture is diluted with water and the mixture is then extracted with ethyl acetate (3×50 mL). The combined ethyl acetate layer is washed with brine, dried of MgSO$_4$, filtered and concentrated to an oil under reduced pressure. Purification is done by column chromatography with 30% ethyl acetate in hexanes to 40% ethyl acetate in hexanes as the eluent to give the desired product.

f. 2-[(4'-chloro[1,1'-biphenyl]-4-yl)sulfonyl]amino-4-hydroxy-5-[2-thiazolyithio]-pentanoic acid To a solution of 3-[(4'-chloro[1,1'-biphenyl]-4-yl)sulfonyl]amino-[2-oxo-5-(thiazol-2-yl)thio]methyl]-tetrahydrofuran 12e (1.30 g, 2.7 mmol) in water (7 mL) and THF (7 mL) is slowly added lithium hydroxide (0.65 g, 27 mmol). The reaction is stirred for 4 hr, then concentrated to dryness. The reaction mixture is diluted with water and then the mixture is extracted with ethyl ether (2×25 mL) The ethyl ether layer is discarded and the aqueous layer is slowly acidified with 1N HCl to pH 5, and then extracted 3 times with ethyl acetate. The combined ethyl acetate layers are washed with water and brine, dried over MgSO$_4$, filtered and concentrated under reduced pressure. The white solid is then recrystallized with ethyl acetate/hexanes to give the desired product as a white solid.

Example 13

2-[(4'-Bromo[1,1'-biphenyl]-4-yl)sulfonyl]amino-4-hydroxy-5-[2-thiazolylthio]-pentanoic acid a. 4'-Bromobiphenyl-4-sulfonic acid

To a solution of 4-bromobiphenyl (18.6 g, 79.8 mmol) in chloroform (150 mL) is added dropwise chlorosulfonic acid (11.2 g, 96 mmol). A white solid precipitate forms during the addition. The reaction is stirred at room temperature for 6 hr, at which time the precipitate is collected by filtration and the precipitate is then washed with cold chloroform. The product is dried under vacuum to give a white solid product. The product is used without further purification.

b. 4'-Bromobiphenyl-4-sulfonyl chloride

To a solution of 4'-bromobiphenyl-4-sulfonic acid 13a (18.8 g, 78.1 mmol) in thionyl chloride (150 mL) is added a catalytic amount of N,N-dimethylformamide (0.3 mL). The reaction mixture is heated to reflux for 4 hr. The mixture is then cooled to room temperature, and concentrated under reduced pressure. Toluene is then added and the mixture is concentrated under reduced pressure. The solid crude product is then recrystallized with ethyl acetate and hexanes to give the solid desired product.

c. Methyl 2-[4'-(bromo[1',1'-biphenyl-yl)-4-sulfonylamino]-pent-4-enoate

To a solution of allylglycine methyl ester hydrochloride (5 g, 30.2 mmol) in CH$_2$Cl$_2$ (150 mL) at 0° C. is added triethylamine (9.2 g, 90.6 mmol), followed by 4-bromobiphenyl-4-sulfonyl chloride 13b (10.5 g, 31.7 mmol) and the mixture is allowed to warm to room temperature and is stirred overnight. The reaction mixture is diluted with water, extracted 3 times with ethyl acetate. The combined ethyl acetate layer is washed with 1 N HCl and brine. The organic layers are dried with MgSO$_4$, filtered, and concentrated to an oil which is allowed to stand and solidifies to the desired product.

d. Methyl 2-[(4'-bromo[1,1'-biphenyl]-4-yl)-sulfonyl]amino-4,5-epoxypentaneoate To a solution of methyl 2-[(4'-bromo[1,1'-biphenyl]-4-yl)-sulfonylamino]-pent-4-eneoate 13c (10.2 g, 24.1mmol) in CH$_2$Cl$_2$ (150 mL), NaHCO3 (11.0 g, 50 mmol) and water (140 mL) at 0° C., is slowly added m-chloroperbenzoic acid (57–86%) (19.4 g, ~80 mmol). The reaction is stirred for 72 hours. The mixture is diluted with aqueous NaHCO$_3$ and this mixture is extracted with ethyl acetate (3×250 mL). The combined ethyl acetate layer is washed with brine, dried over MgSO$_4$, filtered and concentrated to an oil. Purification of this compound is accomplished by column chromatography with 40% ethyl acetate in hexanes as the eluent to give the desired product.

e. 3-[(4'-Bromo[1,1'-biphenyl]-4-yl)sulfonyl]amino-[2-oxo-5-(thiazol-2-yl)thio]methyl]-tetrahydrofuran To a solution of methyl 2-[(4'-bromo[1,1'-biphenyl]-4-yl]amino-4,5-epoxypentaneoate 13d (2.4 g, 5.4 mmol) in benzene (20 mL) and triethylamine (0.96 mL, 6.9 mmol) at room temperature is added slowly 2-mercaptothiazole (1.23 g, 10.5 mmol). The reaction is stirred overnight at room temperature. The resulting mixture is diluted with water and the mixture is then extracted with ethyl acetate (3×50 mL). The combined ethyl acetate layer is washed with brine, dried of MgSO$_4$, filtered and concentrated to an oil under reduced pressure. Purification is done by column chromatography with 30% ethyl acetate in hexanes to 40% ethyl acetate in hexanes as the eluent to give the desired product.

f. 2-[(4'-bromo[1,1'-biphenyl]-4-yl)sulfonyl]amino-4-hydroxy-5-[2-thiazolylthiol-pentanoic acid To a solution of 3-[(4'-bromo[1,1'-biphenyl]-4-yl)sulfonyl]amino-[2-oxo-5-(thiazol-2-yl)thio]methyl]- tetrahydrofuran 13e (1.58 g, 3.1 mmol) in water (8 mL) and THF (8 mL) is slowly added lithium hydroxide (0.74 g, 31 mmol). The reaction is stirred for 4 hr, then concentrated to dryness. The reaction mixture is diluted with water and then the mixture is extracted with ethyl ether (2×25 mL) The ethyl ether layer is discarded and the aqueous layer is slowly acidified with 1N HCl to pH 5, and then extracted 3 times with ethyl acetate. The combined ethyl acetate layers are washed with water and brine, dried over $MgSO_4$, filtered and concentrated under reduced pressure. The white solid is then recrystallized with ethyl acetate hexanes to give the desired product as a white solid.

Example 14

2-[(4'-Trifluoromethyl[1,1'-biphenyl]-4-yl)sulfonyl] amino-4-hydroxy-5-[2-thiazolylthiol-pentanoic acid a. Methyl 2-[(4'-trifluoromethyl[1,1'-biphenyl]-4-yl] amino-4-penteneoate To a solution of methyl 2-[4-(bromophenyl)sulfonyl] amino-4-pentenoate (3.2 g, 9.1 mmol) in benzene (80 mL), $NaHCO_3$ (2.08 g, 20 mmol), and 10 mL of water, is slowly added tetrakis (triphenylphosphine)palladium (0) (0.034 g, 0.03 mmol), followed by 4-trifluoromethylphenylboronic acid (2.8 g, 14.6 mmol). The reaction is stirred and heated to reflux and it is refluxed overnight. The reaction mixture is allowed to cool to room temperature. 1 N HCl (20 mL) is then added to the reaction and stirred and the mixture is then diluted with water. The mixture is extracted with ethyl acetate three times. The combined ethyl acetate layers are washed with brine, dried over $MgSO_4$, filtered and concentrated under reduced pressure to a solid. Purification is done by column chromatography with 30% ethyl acetate in hexane as the eluent to give the desired product.

b. Methyl 2-[(4'-trifluoromethyl[1,1'-biphenyl]-4-yl] amino-4,5-epoxypentaneoate To a solution of methyl 2-[(4'-trifluoromethyl[1,1'-biphenyl]-4-yl]amino-4-penteneoate 14a (3.5 g, 8.4 mmol) in $CH_2Cl_2$ (50 mL), $NaHCO_3$ (2.6 g, 25.2 mmol) and water (30 mL) at 0° C., is slowly added m-chloroperbenzoic acid (57–86%) (7.3 g, 30 mmol). The reaction is stirred for 72 hours. The mixture is diluted with aqueous $NaHCO_3$ and this mixture is extracted with ethyl acetate (3×250 mL). The combined ethyl acetate layer is washed with brine, dried over $MgSO_4$, filtered and concentrated to an oil. Purification of this compound is accomplished by column chromatography with 40% ethyl acetate in hexanes as the eluent to give the desired product.

c. 3-[(4'-Trifluoromethyl[1,1'-biphenyl]-4-yl) sulfonyl[amino[2-oxo-5-(thiazol-2-yl)thio]methyl]- tetrahydrofuran To a solution of methyl 2-[(4'-trifluoromethyl[1,1'-biphenyl]-4-yl]amino-4,5-epoxypentaneoate 14b (1.76 g, 4.1 mmol) in benzene (15 mL) and triethylamine (0.74 mL, 5.3 mmol) at room temperature is added slowly 2-mercaptothiazole (0.96 g, 8.2 mmol). The reaction is stirred overnight at room temperature. The resulting mixture is diluted with water and the mixture is then extracted with ethyl acetate (3×50 mL). The combined ethyl acetate layer is washed with brine, dried of $MgSO_4$, filtered and concentrated to an oil under reduced pressure. Purification is done by column chromatography with 30% ethyl acetate in hexanes to 40% ethyl acetate in hexanes as the eluent to give the desired product.

d. 2-[(4'-Trifluoromethyl[1,1'-biphenyl[-4-yl) sulfonyl[amino-4-hydroxy-5-[2-benzothiazolylthio]- pentanoic acid To a solution of 3-[(4'-trifluoromethyl[1,1'-biphenyl[-4-yl)sulfonyl[amino-[2-oxo-5-(thiazol-2-yl)thio]methyl]- tetrahydrofuran 14c (1.13 g, 2.2 mmol) in water (5 mL) and THF (5 mL) is slowly added lithium hydroxide (0.53 g, 22 mmol). The reaction is stirred for 2 hr, then concentrated to dryness. The reaction mixture is diluted with water and then the mixture is extracted with ethyl ether (2×25 mL) The ethyl ether layer is discarded and the aqueous layer is slowly acidified with 1N HCl to pH 5, and then extracted 3 times with ethyl acetate. The combined ethyl acetate layers are washed with water and brine, dried over $MgSO_4$, filtered and concentrated under reduced pressure. The solid is purified by prep HPLC to give the desired white solid product.

Example 15

2-[(4'-Methoxy[1,1'-biphenyl]-4-yl)sulfonyl]amino- 4-hydroxy-5-(phenylthio)-pentanoic acid a. 3-[(4'-Methoxyl[1,1'-biphenyl]-4-yl)sulfonyl] amino-2-oxo-5-[(phenylthio)methyl]-tetrahydrofuran To a solution of methyl 2-[(4'-methoxy[1,1'-biphenyl]-4-yl)sulfonyl]amino-4,5-epoxypentanoate 1d (0.5 g, 1.28 mmol) in benzene (5 mL) and $Et_3N$ (0.23 mL, 1.66 mmol) at room temperature is added slowly benzenethiol (0.33 mL, 3.2 mmol). The reaction mixture is stirred overnight. The resulting mixture is diluted with water, and then the mixture is extracted three times with EtOAc. The combined EtOAc layer is washed with water, brine, dried over $MgSO_4$, and concentrated to an oil which is purified by column chromatography eluting with EtOAc/hexane (3:7) to give the desired product as a mixture of two isomers (ratio: 4:1).

b. 2-[(4'-Methoxy[1,1'-biphenyl]-4-yl)sulfonyl] amino-4-hydroxy-5-(phenylthio)-pentanoic acid To a solution of 3-[(4'-methoxy[1,1'-biphenyl]-4-yl) sulfonyl]amino-2-oxo-5-[(phenylthio)methyl]- tetrahydrofuran 12a (0.26 g, 0.55 mmol) in water (5 mL) and THF (5 mL) is added slowly lithium hydroxide monohydrate (230 mg, 5.5 mmol). The reaction mixture is stirred overnight, and then concentrated to dryness. The resulting mixture is diluted with water, and then the mixture is extracted twice with $Et_2O$. The $Et_2O$ layer is discarded and the aqueous layer is neutralized carefully with 1N HCl to pH 6, then extracted three times with EtOAc. The combined EtOAc layer is washed with brine, dried over $MgSO_4$ and concentrated to a solid which is recrystallized from EtOAc/ hexane to give the desired product as a white solid.

Example 16

2-[[(1,1'-biphenyl)-4-yl]sulfonyl]amino-4-hydroxy- 5-(phenylthio)-pentanoic acid a. Methyl 2-[[(1,1'-biphenyl)-4-yl]sulfonyl]amino-4- pentenoate To a solution of N-Boc-allylglycine methyl ester 1a (4.0 g, 17.6 mmol) in $CH_2Cl_2$ (15 mL is added trifluoroacetic acid (10 mL) slowly, and the resulting mixture is stirred overnight at room temperature. The reaction mixture is concentrated under reduced pressure to dryness then dissolved in dioxane (15 mL) and water (15 mL). To the solution is added triethyl amine (9.8 mL, 70.4 mmol), followed by biphenyl-4-sulfonyl chloride (5.9 g, 21.12 mmol) and the mixture is stirred overnight. The reaction mixture is diluted with water, extracted three times with EtOAc. The combined EtOAc layer is washed with 1 N HCl, H₂O, brine, dried, and concentrated to an oil which solidified upon standing. The crude product is recrystallized from EtOAc/hexane to give the desired product.

b. Methyl 2-[[(1,1'-biphenyl)-4-yl]sulfonyl]amino-4, 5-epoxypentanoate

To a solution of methyl 2-[[(1,1'-biphenyl)-4-yl]sulfonyl] amino-4-pentenoate 16a (2.0 g, 5.8 mmol) in CH₂Cl₂ (15 mL), NaHCO₃ (0.58 g, 7 mmol) and water (10 mL) at 0° C., is added slowly m-chloroperbenzoic acid (3.3 g, 11.6 mmol, 57–86%). The reaction mixture is stirred overnight. The resulting mixture is diluted with aqueous NaHCO₃, and the mixture is extracted three times with CH₂Cl₂. The combined CH₂Cl₂ layers are washed with NaHCO₃, brine, dried over MgSO₄ and concentrated to an oil which is purified by column chromatography eluting with EtOAc/hexane (4:6) to give the desired product as a mixture of two isomers (ratio 2:3).

c. 3-[[(1,1'-Biphenyl)-4-yl]sulfonyl]amino-2-oxo-5-[(phenylthio)methyl]-tetrahydrofuran To a solution of methyl 2-[[(1,1'-biphenyl)-4-yl]sulfonyl] amino-4,5-epoxypentanoate 16b (0.36 g, 1.47 mmol) in benzene (5 mL) and Et₃N (0.27 g, 1.91 mmol) at room temperature is added slowly benzenethiol (0.38 mL, 3.67 mmol). The reaction mixture is stirred for 3 hrs. The resulting mixture is diluted with water, and then the mixture is extracted three times with EtOAc. The combined EtOAc layer is washed with water, brine, dried over MgSO₄ and concentrated to an oil which is purified by column chromatography eluting with EtOAc/hexane (1:4 to 3:7) to give the desired product as a mixture of two isomers (ratio: ~2:1).

d. 2-[[(1,1'-Biphenyl)-4-yl]sulfonyl]amino-4-hydroxy-5-(phenylthio)-pentanoic acid To a solution of 3-[[(1,1'-biphenyl)-4-yl]sulfonyl]amino-2-oxo-5-[(phenylthio)methyl]-tetrahydrofuran 16c (0.18 g, 0.41 mmol) in water (5 mL) and THF (5 mL) is added slowly lithium hydroxide monohydrate (172 mg, 4.1 mmol). The reaction mixture is stirred for 3 hr, then concentrated to dryness. The resulting mixture is diluted with water, and then the mixture is extracted twice with Et₂O. The Et₂O layer is discarded and the aqueous layer is neutralized carefully with 1N HCl to pH 6, then extracted three times with EtOAc. The combined EtOAc layer is washed with brine, dried over MgSO₄ and concentrated to a solid which is recrystallized from EtOAc/hexane to give the desired product.

Example 17

2-[(4'-Methoxy[1,1'-biphenyl]-4-yl)sulfonyl]amino-4-hydroxy-5-(benzylthio)-pentanoic acid a. 3-[(4'-Methoxy[1,1'-biphenyl]-4-yl)sulfonyl] amino-2-oxo-5-[(benzylthio)methyl]-tetrahydrofuran To a solution of methyl 2-[(4'-methoxy[1,1'-biphenyl]-4-yl)sulfonyl]amino-4,5-epoxypentanoate 1d (0.5 g, 1.28 mmol) in benzene (3 mL), NaHCO₃ (0.32 g, 3.84 mmol) and Et₃N (0.23 mL, 1.6 mmol) at room temperature is added slowly benzyl mercaptan (0.62 mL, 4.99 mmol). The reaction mixture is heated at 70° C. for 3 h, and stirred two days at room temperature. The resulting mixture is diluted with water, and then the mixture is extracted three times with EtOAc. The combined EtOAc layer is washed with water, brine, dried over MgSO₄ and concentrated to an oil which is purified by column chromatography eluting with hexane/EtOAc (4:1) to give the desired product.

b. 2-[(4'-Methoxy[1,1'-biphenyl]-4-yl)sulfonyl] amino-4-hydroxy-5-(benzylthio)-pentanoic acid To a solution of 3-[(4'-methoxy[1,1'-biphenyl]-4-yl) sulfonyl]amino-2-oxo-5-[(benzylthio)methyl]-tetrahydrofuran 17a (40 mg, 0.083 mmol) in water (3 mL) and THF (3 mL) is added slowly lithium hydroxide monohydrate (35 mg, 0.82 mmol). The reaction mixture is stirred overnight, then concentrated to dryness. The resulting mixture is diluted with water, and then the mixture is extracted twice with Et₂O. The Et₂O layer is discarded and the aqueous layer is neutralized carefully with 1N HCl to pH 6, then extracted three times with EtOAc. The combined EtOAc layer is washed with brine, dried over MgSO₄ and concentrated to a solid which is recrystallized from EtOAc/hexane (1:4) to give the desired product as a white solid.

Example 18

2-[(4'-Methoxy[1,1'-biphenyl]-4-yl)sulfonyl]amino-4-hydroxy-5-[(benzyl)sulfonyl]-pentanoic acid To a stirred solution of 2-[(4'-methoxy[1,1'-biphenyl]-4-yl)sulfonyl]amino-4-hydroxy-5-(benzylthio)-pentanoic acid 17b (0.57 g, 1.13 mmol) in CH₂Cl₂ (10 mL) is added slowly peracetic acid (0.55 mL, 2.32 mmol). The reaction is stirred until analytical HPLC showed the starting material is gone. After stirring overnight, water is added to dilute the reaction mixture. The mixture is extracted with ethyl acetate (3×25 mL). The combined ethyl acetate layer is washed with brine, dried with MgSO₄, filtered, and concentrated under reduced pressure to a white solid. Purification is accomplished by prep HPLC to give the desired product as a white solid.

Example 19

2-[(4'-Methoxy[1,1'-biphenyl]-4-yl)sulfonyl]amino-4-hydroxy-5-(phenylamino)-pentanoic acid a. 3-[(4'-Methoxy[1,1'-biphenyl]-4-yl)sulfonyl] amino-2-oxo-5-[(phenylamino)methyl]-tetrahydrofuran To a solution of methyl 2-[(4'-methoxy[1,1'-biphenyl]-4-yl)sulfonyl]amino-4,5-epoxypentanoate 1d (0.5 g, 1.28 mmol) in aniline (0.17 mL, 1.92 mmol) is added magnesium perchlorate (2 mg, 0.009 mmol) and the resulting mixture is heated for 4 h at 80° C. The resulting mixture is cooled to room temperature, and then the mixture is diluted with water, and extracted three times with EtOAc. The combined EtOAc layer is washed with water, brine, dried over MgSO₄ and concentrated to an oil which is purified by column chromatography eluting with hexane/EtOAc (7:3) to give the desired product.

b. 2-[(4'-Methoxy[1,1'-biphenyl]-4-yl)sulfonyl] amino-4-hydroxy-5-(phenylamino)-pentanoic acid To a solution of 3-[(4'-Methoxy[1,1'-biphenyl]-4-yl) sulfonyl]amino-2-oxo-5-[(phenylamino)methyl]-tetrahydrofuran 19a (0.19 g, 0.42 mmol) in water (3 mL) and THF (3 mL) is added slowly lithium hydroxide monohydrate (180 mg, 4.2 mmol). The reaction mixture is stirred for 4 h, and then concentrated to dryness. The resulting mixture is diluted with water, and then the mixture is extracted twice with Et$_2$O. The Et$_2$O layer is discarded and the aqueous layer is neutralized carefully with 1N HCl to pH 6, then extracted three times with EtOAc. The combined EtOAc layer is washed with brine, dried over MgSO$_4$ and concentrated to a solid which is recrystallized from EtOAc/hexane (3:7) to give the desired product as a white solid.

Example 20

2-[(4'-Methoxy[1,1'-biphenyl]-4-yl)sulfonyl]amino-4-hydroxy-5-[(1H-1,2,4-triazol-3yl)thio]-pentanoic acid a. 3-[(4'-Methoxy[1,1'-biphenyl]-4-yl)sulfonyl]amino-2-oxo-5[(1H-1,2,4-triazol-3-ylthio)methyl]-tetrahydrofuran To a solution of methyl 2-[(4'-methoxy[1,1'-biphenyl]-4-yl)sulfonyl]amino-4,5-epoxypentanoate 1d (0.7 g, 1.79 mmol) in benzene (6 mL) and Et$_3$N (0.33 mL, 2.3 mmol) at room temperature is added slowly 1H-1,2,4-mercaptotriazole (0.47 g, 4.48 mmol). The reaction mixture is stirred overnight at room temperature. Diluted with water, the mixture is extracted three times with EtOAc. The combined EtOAc layer is washed with water, brine, dried over MgSO$_4$ and concentrated to an oil which is purified by column chromatography eluting with hexane/EtOAc (1:1) to give the desired product.

b. 2-[(4'-Methoxy[1,1'-biphenyl]-4-yl)sulfonyl]amino-4-hydroxy-5-[(1H-1,2,4-triazol-3-yl)thio]-pentanoic acid To a solution of 3-[(4'-methoxy[1,1'-biphenyl]-4-yl)sulfonyl]amino-2-oxo-5-[(1H-1,2,4-triazol-3-ylthio)methyl]-tetrahydrofuran 20a (0.34 g, 0.68 mmol) in water (5 mL) and THF (5 mL) is added slowly lithium hydroxide monohydrate (290 mg, 4.2 mmol). The reaction mixture is stirred for 4 h, then concentrated to dryness. Diluted with water, the mixture is extracted twice with Et$_2$O. The Et$_2$O layer is discarded and the aqueous layer is neutralized carefully with 1N HCl to pH 6, then extracted three times with EtOAc. The combined EtOAc layer is washed with brine, dried over MgSO$_4$ and concentrated to a solid which is recrystallized from EtOAc/hexane (1:4) to give the desired product as a white solid.

Example 21

2-[(4'-Methoxy[1,1'-biphenyl]-4-yl)sulfonyl]amino-4-hydroxy-5-(phenylamino)-pentanoic acid Example 21 is prepared from N-methylaniline and 1d using the procedure described for compound 19.

Example 22

2-[(4'-Methoxy[1,1'-biphenyl-]-4-yl)sulfonyl]amino-4-hydroxy-5-[(2-imidazolyl)thio]-pentanoic acid Example 22 is prepared from 2-mercaptoimidazole and 1d using the procedure described for compound 20.

Example 23

2-[(4'-Methoxy[1,1'-biphenyl]-4-yl)sulfonyl]amino-4-hydroxy-5-[[2-(5-methylbenzimidazolyl)]thio]-pentanoic acid Example 23 is prepared from 2-mercapto-5-benzimidazole and 1d using the procedure described for compound 20.

Example 24

2-[(4'-Methoxy[1,1'-biphenyl]-4-yl)sulfonyl]amino-4-hydroxy-5-[(4(3H)-quinazolinonyl)thio]-pentanoic acid Example 24 is prepared from 2-mercapto-4(3H)-quinazolinone and 1d using the procedure described for compound 20.

Example 25

2-[(4'-Methoxy[1,1'-biphenyl]-4-yl)sulfonyl]amino-4-hydroxy-5-[(6-ethoxy-2-benzothiazolyl)thio]-pentanoic acid Example 25 is prepared from 6-ethoxy-2-mercaptobenzothiazole and 1d using the procedure described for compound 20.

Example 26

2-[(4'-Methoxy[1,1'-biphenyl]-4-yl)sulfonyl]amino-4-hydroxy-5-[2-benzothiazolylthio]-pentanoic acid Example 26 is prepared from 2-mercaptobenzothiazole and 1d using the procedure described for compound 20.

Example 27

2-[(4'-Methoxy[1,1'-biphenyl]-4-yl)sulfonyl]amino-4-hydroxy-5-[2-benzoxazolylthio]-pentanoic acid Example 27 is prepared from 2-mercaptobenzoxazole and 1d using the procedure described for compound 20.

Example 28

2-[(4'-Methoxy[1,1'-biphenyl]-4-yl)sulfonyl]amino-4-hydroxy-5-[2-benzimidazolylthio]-pentanoic acid Example 28 is prepared from 2-mercaptobenzimidazole and 1d using the procedure described for compound 20.

Example 29

2-[(4'-Methoxy[1,1'-biphenyl]-4-yl)sulfonyl]amino-4-hydroxy-5-[2-(1-methyl-1H-imidazol-2-yl)thio]-pentanoic acid Example 29 is prepared from 2-mercapto-1-methylimidazole and 1d using the procedure described for compound 20.

Example 30

2-[(4'-Methoxy[1,1'-biphenyl]-4-yl)sulfonyl]amino-4-hydroxy-5-[(1-methyl-1H-tetrazol-5-yl)thio]-pentanoic acid Example 30 is prepared from 5-mercapto-1-methyltetrazole and 1d using the procedure described for compound 20.

Example 31

2-[(4'-Methoxy[1,1'-biphenyl]-4-yl)sulfonyl]amino-4-hydroxy-5-[(5-methyl-1,3,4-thiadiazol-2-yl)thio]-pentanoic acid Example 31 is prepared from 5-methyl-1,3,4-thiadiazole-2-thiol and 1d using the procedure described for compound 20.

Example 32

2-[(4'-Methoxy[1,1'-biphenyl]-4-yl)sulfonyl]amino-4-hydroxy-5-[(4-methyl-4(H)-1,2,4-triazol-3-yl)thio]-pentanoic acid Example 32 is prepared from 4-methyl-4H-1,2,4-triazole-3-thiol and 1d using the procedure described for compound 20.

Example 33

2-[(4'-Methoxy[1,1'-biphenyl]-4-yl)sulfonyl]amino-4-hydroxy-5-[(5-(methylthio)-1,3,4-thiadiazol-2-yl)thio]-pentanoic acid Example 33 is prepared from 5-(methylthio)-1,3,4-thiadiazole-2-thiol and 1d using the procedure described for compound 20.

Example 34

2-[(4'-Methoxy[1,1'-biphenyl]-4-yl)sulfonyl]amino-4-hydroxy-5-[2-thienylthio]-pentanoic acid Example 34 is prepared from 2-thiophenethiol and 1d using the procedure described for compound 20.

Example 35

2-[(4'-Methoxy[1,1'-biphenyl-4-yl)sulfonyl]amino-4-hydroxy-5-[(5-phenyl-1,3,4-oxadiazol-2-yl)thio]-pentanoic acid Example 35 is prepared from 5-phenyl-1,3,4-oxadiazole-2-thiol and 1d using the procedure described for compound 20.

Example 36

2-[(4'-Methoxy[1,1'-biphenyl]-4-yl)sulfonyl]amino-4-hydroxy-5-(1-(4-methoxyphenyl)-1H-tetrazol-1-yl)thio]-pentanoic acid Example 36 is prepared from 5-mercapto-1-(4-methoxyphenyl)-1H-tetrazole and 1d using the procedure described for compound 20.

Example 37

2-[(4'-Methoxy[1,1'-biphenyl]-4-yl)sulfonyl]amino-4-hydroxy-5-[(6-chloro-2-benzoxazolyl)thio]-pentanoic acid Example 37 is prepared from 6-chloro-2-benzoxazolethiol and 1d using the procedure described for compound 20.

Example 38

2-[(4'-Methoxy[1,1'-biphenyl]-4-yl)sulfonyl]amino-4-hydroxy-5-[[3-(methylthio)-1,2,4-thiadiazol-5-yl]thio]-pentanoic acid Example 38 is prepared from 3-methylmercapto-5-mercapto-1,2,4-thiadiazole and 1d using the procedure described for compound 20.

Example 39

2-[(4'-Methoxy[1,1'-biphenyl]-4-yl)sulfonyl]amino-4-hydroxy-5-[[5-(4-pyridinyl)-1,3,4-oxadiazol-2-yl]thio]-pentanoic acid Example 39 is prepared from 5-(4-pyridinyl)-1,3,4-oxadiazole-2-thiol and 1d using the procedure described for compound 20.

Example 40

2-[(4'-Methoxy[1,1'-biphenyl]-4-yl)sulfonyl]amino-4-hydroxy-5-[(5-methoxybenzothiazoly-2-yl)thio]-pentanoic acid Example 40 is prepared from 2-mercapto-5-methoxybenzothiazole and 1d using the procedure described for compound 20.

Example 41

2-[(4'-Methoxy[1,1'-biphenyl]-4-yl)sulfonyl]amino-4-hydroxy-5-[(5-methoxy-benzimidazol-2-yl)thio]-pentanoic acid Example 41 is prepared from 5-methoxy-2-benzimidazolethiol and 1d using the procedure described for compound 20.

Example 42

2-[(4'-Methoxy[1,1'-biphenyl]-4-yl)sulfonyl]amino-4-hydroxy-5-[(5-phenyl-1H-1,2,4-triazol-3-yl)thio]-pentanoic acid Example 42 is prepared from 5-phenyl-1H-1,2,4-triazole-3-thiol and 1d using the procedure described for compound 20.

Example 43

2-[(4'-Methoxy[1,1'-biphenyl[-4-yl)sulfonyl]amino-4-hydroxy-5-[(2-methyl-3-furanyl)thio]-pentanoic acid Example 43 is prepared from 2-methyl-3-furanthiol and 1d using the procedure described for compound 20.

Example 44

2-[(4'-Methoxy[1,1'-biphenyl]-4-yl)sulfonyl]amino-4-hydroxy-5-[(4-methoxyphenyl)thio]-pentanoic acid Example 44 is prepared from 4-methoxybenzenethiol and 1d using the procedure described for compound 20.

Example 45

2-[(4'-Methoxy[1,1'-biphenyl]-4-yl)sulfonyl]amino-4-hydroxy-5-[pyrimidin-2-ylthio]-pentanoic acid Example 45 is prepared from 2-mercaptopyrimidine and 1d using the procedure described for compound 20.

Example 46

2-[(4'-Methoxy[1,1'-biphenyl]-4-yl)sulfonyl]amino-4-hydroxy-5-[4,6-dimethylpyrimidin-2-ylthio]-pentanoic acid Example 46 is prepared from 4,6-dimethyl-2-mercaptopyrimidine and 1d using the procedure described for compound 20.

Example 47

2-[(4'-Methoxy[1,1'-biphenyl]-4-yl)sulfonyl]amino-4-hydroxy-5-[pyridin-2ylthio]-pentanoic acid Example 47 is prepared from 2-mercaptopyridine and 1d using the procedure described for compound 20.

Example 48

2-[(4'-Methoxy[1,1'-biphenyl]-4-yl)sulfonyl]amino-4-hydroxy-5-[purin-2-ylthio]-pentanoic acid Example 48 is prepared from 2-mercaptopurine and 1d using the procedure described for compound 20.

Example 49

2-[(4'-Methoxy[1,1'-biphenyl]-4-yl)sulfonyl]amino-4-hydroxy-5-[4-methylcoumarin-7-ylthio]-pentanoic acid Example 49 is prepared from 7-mercapto-4-methylcoumarin and 1d using the procedure described for compound 20.

Example 50

2-[(4'-Methoxy[1,1'-biphenyl]-4-yl)sulfonyl]amino-4-hydroxy-5-[[(4-methoxyphenyl)methyl]thio]-pentanoic acid Example 50 is prepared from 4-methoxy-α-toluenethiol and 1d using the procedure described for compound 20.

Example 51

2-[(4'-Methoxy[1,1'-biphenyl]-4-yl)sulfonyl]amino-4-hydroxy-5-[[(4-fluorophenyl)methyl]thio]-pentanoic acid Example 51 is prepared from 4-fluorobenzylmercaptan and 1d using the procedure described for compound 20.

Example 52

2-[(4'-Methoxy[1,1'-biphenyl]-4-yl)sulfonyl]amino-4-hydroxy-5-[furfurylthio]-pentanoic acid Example 52 is prepared from furfuryl mercaptan and 1d using the procedure described for compound 20.

Example 53

2-[(4'-Methoxy[1,1'-biphenyl]-4-yl)sulfonyl]amino-4-hydroxy-5-](2-thienyl)methylthio]-pentanoic acid Example 53 is prepared from 2-thienylmercaptan and 1d using the procedure described for compound 20.

Example 54

2-[(4'-Methoxy[1,1'-biphenyl]-4yl)sulfonyl]amino-4-hydroxy-5-phenoxypentanoic acid Example 54 is prepared from phenol and 1d using the procedure described for compound 20.

Example 55

2-[(4'-Methoxy[1,1'-biphenyl]-4-yl)sulfonyl]amino-4-hydroxy-5-[pyridin-3-yloxy]-pentanoic acid Example 55 is prepared from 3-hydroxypyridine and 1d using the procedure described for compound 20.

Example 56

2-[(4'-Methoxy[1,1'-biphenyl]-4-yl)sulfonyl]amino-4-hydroxy-5-[pyrimidin-2-yloxy]-pentanoic acid Example 56 is prepared from 2-hydroxypyrimidine and 1d using the procedure described for compound 20.

Example 57

2-[(4'-Methoxy[1,1'-biphenyl]-4-yl)sulfonyl]amino-4-hydroxy-4-methyl-5-[-(1-N-methyl-imidazol-2-yl-thio)-methyl]-pentanoic acid a. Methyl 2-[(4'-Methoxy[1,1'-biphenyl]-4-yl) sulfonyl]amino-4-methylpent-4-enoate The starting methyl 2-tert-butoxycarbonylamino-4-methylpent-4-enoate (6.0 g, 24.7 mmol; *Tetrahedron* 1997, 33, 88; *Tetrahedron Lett* 1994, 3669) is taken in 100 mL of methylene chloride, treated with 10 mL of trifluoroacetic acid, stirred for three hr., evaporated to dryness and triturated twice with chloroform. The residue is then taken in 210 mL of methylene chloride in the presence of 21 mL of triethylamine, treated with (4'-Methoxy[1,1'-biphenyl]-4-yl) sulfonyl chloride, stirred for three days and concentrated. The residue is then partitioned between EtOAc and 1N HCl and the organic layer is washed with 1N HCl, washed with brine, dried over $MgSO_4$, filtered and evaporated. The resulting material is then purified over flash silica with hexanes:EtOAc (7:3) to give a white solid.

b. Methyl 2-[(4'-Methoxy[1,1'-biphenyl]-4-yl) sulfonyl]amino-4-methyl-4,5-epoxy-pentanoate The starting olefin 57a (2.6 g, 6.68 mmol) is taken in methylene chloride and treated with meta-chloroperoxybenzoic acid (4.7 g, 27 mmol). The resulting solution is stirred for 18 hr., diluted with methylene chloride, washed 2 times with dilute $Na_2CO_3$, dried over $MgSO_4$, filtered and evaporated to give a solid residue which is purified over flash silica with hexanes:EtOAc (7:3) to give a white solid.

c. 3-[(4'-Methoxy[1,1'-biphenyl]-4-yl)sulfonyl] amino-2-oxo-5-methyl-5-[(1-N-Methyl-imidazol-2-yl-thio)-methyl]-tetrahydrofuran The starting epoxide 57b is opened with 1-N-methyl-2-mercaptoimidazole as described for compound 1e to give a white solid.

d. The starting ester 57c is hydrolyzed as described for compound 1f to give the title acid as a white solid.

Example 58

2-[(4'-Methoxy[1,1'-biphenyl]-4-yl)sulfonyl]amino-4-hydroxy-4-methyl-5-[(thiazol-2-yl)-thiomethyl]-pentanoic acid The starting epoxide 57b is opened with 2-mercaptothiazol as described for compound 1e and the resulting product is hydrolyzed as described for compound 1f to give the title acid as a white solid.

Example 59

2-[(4'-Methoxy[1,1'-biphenyl]-4-yl)sulfonyl]amino-4-hydroxy-4-methyl-5-[(1H-1,2,4-triazol-5-yl)-thiomethyl]-pentanoic acid The starting epoxide 57b is opened with 5-mercapto-1H-1,2,4-triazole as described for compound 1e and the resulting product is hydrolyzed as described for compound 1f to give the title acid as a white solid.

Example 60

2-[(4'-Methoxy[1,1'-biphenyl]-4yl)sulfonyl]amino-4-hydroxy-4-methyl-5-[(3-trifluoromethylpyridin-2-yl)-thiomethyl]-pentanoic acid The starting epoxide 57b is opened with 2-mercapto-3-trifluoromethylpyridin as described for compound 1e and the resulting product is hydrolyzed as described for compound 1f to give the title acid as a white solid.

Example 61

2-[(4'-Methoxy[1,1'-biphenyl]-4-yl)sulfonyl]amino-4-hydroxy-5-[(3-triflurromethyl)-2-pyridyl-thio]-pentanoic acid a. 3-[(4'-Methoxy[1,1'-biphenyl]-4-yl)sulfonyl]amino-2-oxo-5-[[(3-trifluoromethyl)-2-pyridyl-thio]methyl]-tetrahydrofuran To a solution of methyl 2-[(4'-methoxy[1,1'-biphenyl]-4-yl]amino-4,5-epoxypentaneoate 1d (1.9 g, 5.1 mmol) in benzene (25 mL) and triethylamine (0.99 mL, 7.1 mmol) at room temperature is added slowly 2-mercapto-3-(trifluoromethyl)pyridine (2.29 g, 12.8 mmol). The reaction is stirred overnight at room temperature. The resulting mixture is diluted with water and the mixture is then extracted with ethyl acetate (3×50 mL). The combined ethyl acetate layer is washed with brine, dried of MgSO4, filtered and concentrated to an oil under reduced pressure. Purification is done by column chromatography with 30% ethyl acetate in hexanes to 40% ethyl acetate in hexanes as the eluent to give the desired product.

b. 2-[(4'-Methoxy[1,1'-biphenyl]-4-yl)sulfonyl]amino-4-hydroxy-5-[(3-trifluoromethyl)-2-pyridyl-thio]-pentanoic acid To a solution of 3-[(4'-methoxy[1,1'-biphenyl]-4-yl)sulfonyl]amino-2-oxo-5-[[(3-trifluoromethyl)-2-pyridyl-thio]methyl]-tetrahydrofuran 61a (1.67 g, 3.1 mmol) in water (5 mL) and THF (5 mL) is slowly added lithium hydroxide (0.74 g, 3.1 mmol). The reaction is stirred for 4 hr, then concentrated to dryness. The reaction mixture is diluted with water and then the mixture is extracted with ethy ether (2×25 mL) The ethyl ether layer is discarded and the aqueous layer is slowly acidified with 1N HCl to pH 5, and then extracted 3 times with ethyl acetate. The combined ethyl acetate layers are washed with water and brine, dried over MgSO4, filtered and concentrated under reduced pressure. The compound is purified by HPLC to give the desired product as a white solid.

Example 62

2-[(4'-Methoxy[1,1'-biphenyl]-4-yl)sulfonyl]-N-methyl-amino-4-hydroxy-5-(phenylthio)-pentanoic acid

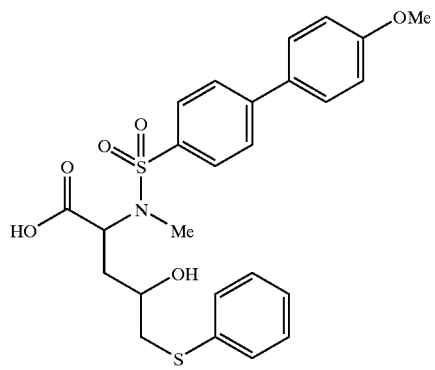

a. Methyl 2-[(4'-methoxy[1,1'-biphenyl]-4-yl]-N-methylamino-4-penteneoate

To a stirred solution of methyl 2-[(4'-methoxy[1,1'-biphenyl]-4-yl]amino-4-penteneoate 1c (3.6 g, 9.6 mmol) in DMF (75 mL) is added Na bis(TMS)amide (1.0 M, 12 mL) followed by methyl iodide (2.04 g, 14.4 mmol) and this mixture is stirred overnight at room temperature. 1 N HCl (25 mL) is then added and the mixture is diluted with water and is extracted with ethyl acetate (3×100 mL). The combined ethyl acetate layer is washed with brine, dried with MgSO4, filtered and concentrated under reduced pressure to the crude product. The crude is purified by column chromatography eluting with 30% ethyl acetate in hexanes to get the desired product.

b. Methyl N-methyl-2-[(4'-methoxy[1,1'-biphenyl]-4-yl]-amino-4,5-epoxypentanoate To a solution of methyl 2-[(4'-methoxy[1,1'-biphenyl]-4-yl]amino-4-penteneoate 62a (1.64 g, 4.2 mmol) in CH$_2$Cl$_2$ (30 mL), NaHCO$_3$ (0.42 g, 5.1 mmol) and water (15 mL) at 0° C., is slowly added m-chloroperbenzoic acid (57–86%) (1.5 g, ~9 mmol). The reaction is stirred for 18 hr. The mixture is diluted with aqueous NaHCO$_3$ and this mixture is extracted with ethyl acetate (3×250 mL). The combined ethyl acetate layer is washed with brine, dried over MgSO$_4$, filtered and concentrated to an oil. Purification of this compound is accomplished by column chromatography with 40% ethyl acetate in hexanes as the eluent to give the desired product.

c. N-Methyl 3-[(4'-Methoxy[1,1'-biphenyl]-4-yl)sulfonyl]amino-2-oxo-5-[[(2-benzothiazolyl)thio]methyl]-tetrahydrofuran To a solution of methyl 2-[(4'-methoxy[1,1'-biphenyl]-4-yl]amino-4,5-epoxypentanoate 62b (1.07 g, 2.65 mmol) in benzene (10 mL) and triethylamine (0.52 mL, 3.7 mmol) at room temperature is added slowly 2-mercaptothiazole (0.78 g, 6.6 mmol). The reaction is stirred overnight at room temperature. The resulting mixture is diluted with water and the mixture is then extracted with ethyl acetate (3×25 mL). The combined ethyl acetate layer is washed with brine, dried of MgSO$_4$, filtered and concentrated to an oil under reduced pressure. Purification is done by column chromatography with 30% ethyl acetate in hexanes to 40% ethyl acetate in hexanes as the eluent to give the desired product.

d. N-Methyl 2-[(4'-Methoxy[1,1'-biphenyl]-4-yl)sulfonyl]amino-4-hydroxy-5-[2-benzothiazolylthio]-pentanoic acid To a solution of N-methyl 3-[(4'-Methoxy[1,1'-biphenyl]-4-yl)sulfonyl]amino-2-oxo-5-[[(2-benzothiazolyl)thio]methyl]-tetrahydrofuran 62c (1.00 g, 2.05 mmol) in water (5 mL) and THF (5 mL) is slowly added lithium hydroxide (0.49 g, 20.5 mmol). The reaction is stirred for 4 hr, then concentrated to dryness. The reaction mixture is diluted with water and then the mixture is extracted with ethy ether (2×25 mL) The ethyl ether layer is discarded and the aqueous layer is slowly acidified with 1N HCl to pH 5, and then extracted 3 times with ethyl acetate. The combined ethyl acetate layers are washed with water and brine, dried over MgSO$_4$, filtered and concentrated under reduced pressure. The white solid is then recrystallized with ethyl acetate/hexanes to give the desired product as a white solid.

Examples 63–67

The following chemical formula along with Table 2 shows the structure of compounds made according to the description in Examples 63–67 described below.

TABLE 2

| Example | R₁ | R₂ | R₃ |
|---|---|---|---|
| 63 | 4-MeO-phenyl | 2-thiazolyl-S- | benzyl |
| 64 | 4-MeS-phenyl | 2-thiazolyl-S- | benzyl |
| 65 | 4-MeO-phenyl | 2-thiazolyl-S- | —H |
| 66 | 4-MeO-phenyl | 4-methyl-4H-1,2,4-triazol-3-yl-S- | benzyl |
| 67 | 4-MeO-phenyl | 4-methyl-4H-1,2,4-triazol-3-yl-S- | —H |

Example 63

2-[(4'-Methoxy[1,1'-biphenyl]-4-yl)sulfonyl]amino-3-phenylmethoxy-4-hydroxy-5-[(2-thiazolyl)thio]-pentanoic acid a. N-[(1,1-Dimethylethoxy)carbonyl]glycine-4phenylmethoxy-2-butenyl ester

N-[(1,1-Dimethylethoxy)carbonyl]glycine (21.9 grams, 0.125 mol), cis-4-benzyloxy-2-buten-1-ol (25 mL, 0.15 mol), and 4-dimethylaminopyridine (1.5 grams, 0.013 mol) are dissolved in methylene chloride and stirred at 0° C. Then N,N-dicyclohexylcarbodiimide (31 grams, 0.15 mol) in 30 mL methylene chloride is added and the reaction is stirred at 0° C. for five minutes. The reaction is then stirred for an additional twelve hours at 25° C. Additional methylene chloride is added and the reaction is washed consecutively with 1 N HCl, sodium bicarbonate and then with brine. The organic extract is dried over magnesium sulfate and the solvent evaporated in vacuo to give an orange oil which is absorbed onto silica gel and applied to a dry silica column. The column is eluted with hexane/EtOAc (9:1) then with hexane/EtOAc (8:2) Product fractions are combined and dried in vacuo to give the desired product.

b. 2-[(1,1-Dimethylethoxy)carbonyl]amino-3-phenylmethoxy-4pentenoic acid

A lithium diisopropylamide solution (37.3 M) is prepared from N,N-diisopropylamine (5.2 mL, 37.2 mmol) in THF (30 mL. cooled to −20° C.) and 3.7 mL (37.3 mmol) 10 M n-BuLi in hexane. The LDA solution in THF is added to a stirred solution of N-[(1,1-dimethylethoxy)carbonyl] glycine-4-phenylmethoxy-2-butenyl ester 63a (14.9 mmol) and ZnCl₂ (17.9 mmol) in 100 mL THF at −78° C. The mixture is allowed to come to room temperature overnight.

The crude mixture is partitioned between 700 mL ethyl acetate and 700 mL 1 N HCl. The organic layer is washed with 150 mL dilute NaHCO$_3$ solution (3×'s). The bicarbonate washes are acidified with conc. HCl to pH1 and extracted with 700 mL ethyl acetate. The ethyl acetate layer is dried over magnesium sulfate and the solvent removed in vacuo to give the named compound.

c. Methyl 2-[4-bromophenylsulfonyl]amino-3-phenylmethoxy-4-pentenoate

The 2-[[1,1-dimethylethoxy)carbonyl]amino-3-phenylmethoxy-4-pentenoic acid 63b (1.8 g, 5.37 mmol) is dissolved in methanol (54 mL) and thionyl chloride (8.3 mL) is added dropwise to the mixture. The resulting mixture is stirred at room temperature until the reaction is complete by tlc. The crude reaction is dried and re-evaporated from methanol (3 times). The dried reaction mixture is taken up in methylene chloride (30 mL) and triethylamine (7 mL). 4-Bromophenylsulfonyl chloride (1.23 g, 4.83 mmol) is added and the reaction is stirred overnight. The solvent is removed in vacuo and the oil is taken up in ethyl acetate, and then washed consecutively with 1N HCl, saturated sodium bicarbonate solution, and finally with brine, then dried over magnesium sulfate and the solvent removed in vacuo. The crude material is adsorbed onto silica gel and purified over a silica column eluting with hexane followed with hexane:ethyl acetate (8:2). Product fractions are combined and dried to give the desired product.

d. Methyl 2-[(4'-methoxy[1,1'-biphenyl]-4-yl)sulfonyl]amino-3-phenylmethoxy-4-pentenoate The methyl 2-[4-bromophenylsulfonyl]amino-3-phenylmethoxy-4-pentenoate 63c (320 mg, 0.683 mmol) is dissolved in benzene (4 mL) and sodium carbonate (148 mg), in water (0.6 mL), is added along with tetrakis(triphenylphosphine)palladium. 4-Methoxyphenylboronic acid (157 mg, 1.03 mmol), in methanol (0.4 mL), is added and the mixture is heat to reflux overnight. Ether is added to the reaction which is washed with water (3 times) and brine, the organic layer is dried over magnesium sulfate and the solvent stripped in vacuo to give the crude product as a yellow solid. The crude material is adsorbed onto silica gel and purified over a silica column eluting with hexane/ethyl acetate (9:1) followed with hexane/ethyl acetate (1/1). Product fractions are combined and dried to give the desired product.

e. Methyl 2-[(4'-methoxy[1,1'-biphenyl]-4-yl)sulfonyl]amino-3-phenylmethoxy-4,5-epoxypentanoate The methyl 2-[(4'-methoxy[1,1'-biphenyl]-4-yl)sulfonyl]amino-3-phenylmethoxy-4-pentenoate 63d (1.23 g, 2.48 mmol) is dissolved in methylene chloride (9 mL) and sodium bicarbonate (252 mg), in water (4 mL), then the reaction is cooled to 0° C. 3-Chloroperoxybenzoic acid is added slowly and the reaction is stirred for two hours. The substrate is still present so additional 3-chloroperoxybenzoic acid is added (1 g) along with 175 mg sodium bicarbonate and the reaction is stirred overnight. The mixture is diluted with aqueous sodium bicarbonate solution and methylene chloride and the layers are separated. The aqueous layer is washed with ethyl acetate (3 times) and the organic layers are combined and dried under reduced pressure. The resulting material is redissolved in ethyl acetate and washed with dilute sodium bicarbonate solution and then with brine, dried over magnesium sulfate and concentrated in vacuo to a light brown oil (2 g). The crude material is adsorbed onto silica gel and purified over a silica column eluting with hexane:ethyl acetate (8:2) followed with hexane:ethyl acetate (1:1). Product fractions are combined and dried to give the desired product.

f. 3-[(4'-Methoxy[1,1'-biphenyl]-4-yl)sulfonyl]amino-2-oxo-4-phenylmethoxy-5-[[(2-thiazolyl)thio]methyl]-tetrahydrofuran The methyl 2-[(4'-methoxy[1,1'-biphenyl]-4-yl)sulfonyl]amino-3-phenylmethoxy-4,5-epoxypentanoate 63e (285 mg, 0.558 mmol) is dissolved in benzene/triethylamine (2.5 mL, 0.101 mmol) and 2-mercaptothiazole (164 mg, 1.40 mmol) is added. The resulting mixture is then stirred at room temperature for four hours. The mixture is diluted with ethyl acetate and water and extracted with ethyl acetate (3 times). The organic layer is washed with water and brine, then dried over magnesium sulfate and concentrated to a clear oil. The crude material is adsorbed onto silica and purified over a silica column eluting with ethyl acetate/hexane (2/8) followed with ethyl acetate/hexane (1/1). Product fractions are combined and the solvent is removed in vacuo to give the desired product as a clear oil.

g. 2-[(4'-Methoxy[1,1'-biphenyl]-4-yl)sulfonyl]amino-3-phenylmethoxy-4-hydroxy-5-[(2-thiazolyl)thio]-pentanoic acid The 3-[(4'-Methoxy[1,1'-biphenyl]-4-yl)sulfonyl]amino-2-oxo-4-phenylmethoxy-5-[[(2-thiazolyl)thio]methyl]-tetrahydrofuran 63f, 154 mg, 0.258 mmol) is dissolved in THF/water (2 mL/2 mL) and lithium hydroxide (108 mg, 2.58 mmol) is added and the reaction is stirred for two hours at room temperature. The reaction is concentrated to remove the solvent, diluted with water and extracted (2 times) with ether. The aqueous layer is neutralized with 1N HCl to pH6 and extracted with ethyl acetate (3 times). The combined organic layer is washed with brine, dried over magnesium sulfate, and the solvent removed in vacuo. The crude material is adsorbed onto silica gel and purified over a short silica column eluting with hexane/ethyl acetate (1/1) followed with ethyl acetate and ethyl acetate/methanol (8/2). Product fractions are combined and dried to give the desired product as a white solid.

Example 64

2-[(4'-Thiomethoxy[1,1'-biphenyl]-4-yl)sulfonyl]amino-3-phenylmethoxy-4-hydroxy-5-[(2-thiazolyl)thio]-pentanoic acid Example 64 is prepared from 4-(methylthio)phenylboronic acid and 63d using the procedure described for compound 63.

Example 65

2-[(4'-Methoxy[1,1'-biphenyl]-4-yl)sulfonyl]amino-3,4-dihydroxy-5-[(2-thiazolyl)thio]-pentanoic acid Example 65 is prepared from compound 63g by hydrogenolysis of the corresponding benzyl ether.

Example 66

2-[(4'-Methoxy[1,1'-biphenyl]-4-yl)sulfonyl]amino-3,4-dihydroxy-5-[(4-methyl-4(H)-1,2,4-triazol-3-yl)thio]-pentanoic acid Example 66 is prepared from compound 63e and 4-methyl-4H-1,2,4-triazole-3-thiol using the procedure described for compound 63.

Example 67
2-[(4'-Methoxy[1,1'-biphenyl]-4-yl)sulfonyl]amino-3,4-dihydroxy-5-[(4-methyl-4(H)-1,2,4-triazol-3-yl)thio]-pentanoic acid Example 67 is prepared from compound 66 by hydrogenolysis of the corresponding benzyl ether.

Examples 68–72

The following chemical formula along with Table 3 shows the structure of compounds made according to the description in Examples 68–72 described below.

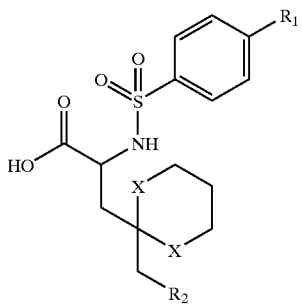

TABLE 3

| Example | R₁ | X | R₃ |
|---|---|---|---|
| 68 | ⟨phenyl⟩-OMe | —O— | ⟨CH₂-O-phenyl⟩ |
| 69 | ⟨phenyl⟩-Br | —O— | ⟨CH₂-O-phenyl⟩ |
| 70 | ⟨phenyl⟩-OMe | —O— | ⟨CH₂-S-phenyl⟩ |
| 71 | ⟨phenyl⟩-OMe | —O— | ⟨CH₂-N(C=O)-azepane⟩ |
| 72 | ⟨phenyl⟩-OMe | —S— | ⟨CH₂-O-phenyl⟩ |

Example 68
2-[(4'-Methoxy-1,1'-biphenyl]-4-yl)-sulfonyl]-amino-3-(2-phenoxymethyl-[1,3]dioxan-2-yl)-propionic acid a Ethyl 2-tert-butoxycarbonylamino-4-oxo-5-bromopentanoate

The starting ethyl 2-tert-butoxycarbonylamino-4-bromopent-4-enoate (1.6 g, 4.57 mmol; *Tetrahedron* 1997, 33, 88; *Tetrahedron Lett* 1994, 3669) is taken in $CH_3CN:H_2O$ (4:1), treated with N-bromosuccinamide (1.06 g, 5.94 mmol) and five drops of 48% HBr and stirred for 3 hr. The mixture is then partitioned between dil. $NaHCO_3$ and hexanes:EtOAc (1:1). The organic layer is washed with brine, dried over MgSO4, filtered and evaporated. The residue is purified over flash silica with hexanes:EtOAc (10:1 to 7:3) to give a pale yellow oil which solidified upon standing.

b. Ethyl 2-tert-butoxycarbonylamino-4-oxo-5phenoxypentanoate

The starting bromoketone 68a (3 g, 8.9 mmol) is taken in 80 mL of THF:DMF (5:3) in the presence of phenol (1.0 g, 10.7 mmol) and 4.7 g of $Na_2CO_3$. The resulting solution is heated to 85° C. for 16 hr, cooled to RT, diluted with EtOAc, washed with water and then dil. $Na_2CO_3$, dried over $MgSO_4$, filtered and evaporated to give a tan oil which is purified over flash silica with hexanes:EtOAc (3:1) to yield a pale yellow oil.

c. Ethyl 2-amino-3-(2-phenoxymethyl-[1,3]dioxan-2-yl)-propionate

The starting ketone 68b (2.14 g, 6.3 mmol) is taken in 20 mL of methylene chloride in the presence of 1,3-dihydroxypropane (2.95 g, 13.4 mmol) and treated with boron trifluoroetherate (2.4 mL, 19.1 mmol). The resulting mixture is allowed to stir for 2 hr, diluted with EtOAc, washed with 1N NaOH, washed with 5% $NH_4Cl$, dried over $MgSO_4$, filtered and evaporated to give a pale yellow oil.

d. Ethyl 2-[(4'-Methoxy-[1,1'-biphenyl]-4-yl)-sulfonyl-amino-3-(2-phenoxymethyl-[1,3]dioxan-2-yl)-propionate

The free amine 68c (982 mg, 3.17 mmol) is taken in 20 mL of $CH_2Cl_2$ in the presence of 2 mL of $NEt_3$, treated with (4'-methoxy-[1,1'-biphenyl]-4-yl)-sulfonyl chloride (1.07 g, 3.81 mmol), stirred for 12 hr and partitioned between EtOAc and 1N HCl. The organic layer is washed with brine, dried over MgSO4, filtered and evaporated to give a yellow solid which is purified over flash silica with hexanes:EtOAc (3:2) to give a white solid.

e. The starting ester 68d is hydrolyzed as described for compound 1f to give the title acid as a white solid.

Example 69
2-[(4'-Bromo-[1,1'-biphenyl]-4-yl)-sulfonyl]-amino-3-(2-phenoxymethyl-[1,3]dioxan-2-yl)-propionic acid The starting free amine 68c is coupled to (4'-Bromo-[1,1'-biphenyl]-4-yl)-sulfonyl chloride and carried forward to the title acid as described for compounds 68c–e.

Example 70
2-[(4'-Methoxy-[1,1'-biphenyl]-4-yl)-sulfonyl]-amino-3-(2-thiophenoxymethyl-[1,3]dioxan-2-yl)-propionic acid The bromoketone 68a is coupled with thiophenol and carried forward to the title acid as described for compounds 68b–e.

Example 71
2-[(4'-Methoxy-[1,1'-biphenyl]-4-yl)-sulfonyl]-amino-3-[2-(2-oxo-azepan-1-ylmethyl)-[1,3]dioxan-2-yl]-propionic acid a. Ethyl 2-tert-butoxycarbonylamino-4-oxo-5-phenoxypentanoate

The starting bromoketone 68a (1.0 g, 3.0 mmol) is dissolved in 1 mL of DMF, treated with 1-aza-2-methoxy-1- cycloheptene (0.518 mL, 3.6 mmol) and heated to 60° C. for 16 hr. The mixture is then dissolved in EtOAc, washed three times with water, dried over Na2SO4, filtered and evaporated to give an amber oil. This material is then purified over flash silica with hexanes:EtOAc (4:6) to give the desired lactam as a yellow oil.

b. The starting lactam 71a is carried forward to the title acid as described for compounds 68c–e.

Example 72

2-[(4'-Methoxy-[1,1'-biphenyl]-4-yl)-sulfonyl]-amino-3-(2-phenoxymethyl-[1,3]dioxan-2-yl)-propionic acid The starting ketone 68c is ketalized with 1,3-propanethiol and carried forward to the title acid as described for compound 68c–d.

IX. Examples—Compositions and Methods of Use

The compounds of the invention are useful to prepare compositions for the treatment of ailments associated with unwanted MP activity. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

The following abbreviations are used in this section:
EDTA: ethylenediaminetetracetic aicd
SDA: synthetically denatured alcohol
USP: United States Pharmacopoeia

Example A

A tablet composition for oral administration, according to the present invention, is made comprising:

| Component | Amount |
| --- | --- |
| The compound of Example 1 | 15 mg |
| Lactose | 120 mg |
| Maize Starch | 70 mg |
| Talc | 4 mg |
| Magnesium Stuart | 1 mg |

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation, and improved mobility without concomitant pain.

Example B

A capsule for oral administration, according to the present invention, is made comprising:

| Component | Amount (% w/w) |
| --- | --- |
| The compound of Example 6 | 15% |
| Polyethylene glycol | 85% |

A human male subject weighing 90 kg (198 lbs.), suffering from osteoarthritis, is treated by a method of this invention. Specifically, for 5 years, a capsule containing 70 mg of the compound of Example 3 is administered daily to said subject.

At the end of the treatment period, the patient is examined via x-ray, arthroscopy and/or MRI, and found to have no further advancement of erosion/fibrillation of the articular cartilage.

Example C

A saline-based composition for local administration, according to the present invention, is made comprising:

| Component | Amount (% w/w) |
| --- | --- |
| The compound of Example 10 | 5% |
| Polyvinyl alcohol | 15% |
| Saline | 80% |

A patient having deep corneal abrasion applies the drop to each eye twice a day. Healing is speeded, with no visual sequelae.

Example D

A topical composition for local administration according to the present invention, is made comprising:

| Component | Composition (% w/v) |
| --- | --- |
| The compound of Example 19 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

A patient suffering from chemical burns applies the composition at each dressing change (b.i.d.). Scarring is substantially diminished.

Example E

An inhalation aerosol composition, according to the present invention, is made comprising:

| Component | Composition (% w/v) |
| --- | --- |
| Compound of Example 42 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

An asthma sufferer sprays 0.01 mL via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 54 | 0.10 |
| Benzalkonium chloride | 0.01 |
| EDTA | 0.05 |
| Hydroxyethylcellulose (NATROSOL M) | 0.50 |
| Sodium metabisulfite | 0.10 |
| Sodium chloride (0.9%) | q.s. |
| Total = | 100.0 |

A human male subject weighing 90 kg (198 lbs), suffering from corneal ulcerations, is treated by a method of this invention. Specifically, for 2 months, a saline solution containing 10 mg of the compound of Example 54 is administered to said subject's affected eye twice-daily.

Example G

A composition for parenteral administration is made comprising:

| Component | Amount |
|---|---|
| The compound of Example 22 | 100 mg/mL carrier |
| Carrier: | |
| Sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 mL of the suspension is administered, via injection, to a human subject with a premetastatic tumor. The injection site juxtaposes the tumor. This dosage is repeated twice daily, for approximately 30 days. After 30 days, symptoms of the disease subside, and dosage is gradually decreased to maintain the patient.

Example H

A mouthwash composition is prepared:

| Component | % w/v |
|---|---|
| The compound of Example 51 | 3.00 |
| SDA 40 Alcohol | 8.00 |
| Flavor | 0.08 |
| Emulsifier | 0.08 |
| Sodium Fluoride | 0.05 |
| Glycerin | 10.00 |
| Sweetener | 0.02 |
| Benzoic acid | 0.05 |
| Sodium hydroxide | 0.20 |
| Dye | 0.04 |
| Water | balance to 100% |

A patient with gum disease uses 1 mL of the mouthwash thrice daily to prevent further oral degeneration.

Example I

A lozenge composition is prepared:

| Component | % w/v |
|---|---|
| The compound of Example 11 | 0.01 |
| Sorbitol | 17.50 |
| Mannitol | 17.50 |
| Starch | 13.60 |
| Sweetener | 1.20 |
| Flavor | 11.70 |
| Color | 0.10 |
| Corn Syrup | balance to 100% |

A patient uses the lozenge to prevent loosening of an implant in the maxilla.

Example J

Chewing Gum Composition

| Chewing Gum Composition | |
|---|---|
| Component | w/v % |
| The compound of Example 9 | 0.03 |
| Sorbitol crystals | 38.44 |
| Paloja-T gum base | 20.00 |
| Sorbitol (70% aqueous solution) | 22.00 |
| Mannitol | 10.00 |
| Glycerine | 7.56 |
| Flavor | 1.00 |

A patient chews the gum to prevent loosening of dentures.

Example K

| Components | w/v % |
|---|---|
| Compound of Example 37 | 4.0 |
| USP Water | 50.656 |
| Methylparaben | 0.05 |
| Propylparaben | 0.01 |
| Xanthan Gum | 0.12 |
| Guar Gum | 0.09 |
| Calcium carbonate | 12.38 |
| Antifoam | 1.27 |
| Sucrose | 15.0 |
| Sorbitol | 11.0 |
| Glycerin | 5.0 |
| Benzyl Alcohol | 0.2 |
| Citric Acid | 0.15 |
| Coolant | 0.00888 |
| Flavor | 0.0645 |
| Colorant | 0.0014 |

The composition is prepared by first mixing 80 kg of gylcerin and all of the benzyl alcohol and heating to 65° C., then slowly adding and mixing together methylparaben, propylparaben, water, xanthan gum, and guar gum. Mix these ingredients for about 12 minutes with a Silverson in-line mixer. Then slowly add in the following ingredients in the following order: remaining glycerin, sorbitol, antifoam C, calcium carbonate, citric acid, and sucrose. Separately combine flavors and coolants and then slowly add to the other ingredients. Mix for about 40 minutes. The patient takes the formulation to prevent flare up of colitis.

Example L

An obese human female subject, who is determined to be prone to osteoarthritis, is administered the capsule described in Example B to prevent the symptoms of osteoarthritis. Specifically, a capsule is administered daily to the subject.

The patient is examined via x-ray, arthroscopy and/or MRI, and found to have no significant advancement of erosion/fibrillation of the articular cartilage.

Example M

A human male subject weighing 90 kg (198 lbs.), who suffers a sports injury to the knee, is administered the capsule described in Example B to prevent the symptoms of osteoarthritis. Specifically, a capsule is administered daily to the subject.

The patient is examined via x-ray, arthroscopy and/or MRI, and found to have no significant advancement of erosion/fibrillation of the articular cartilage.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to Formula (I)

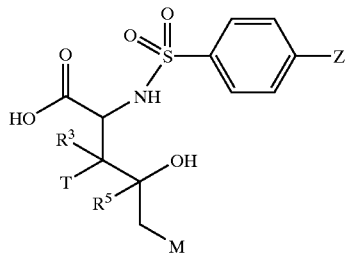

(I)

wherein (A) $R^3$ is selected from the group consisting of hydrogen and alkyl;

(B) T is selected from the group consisting of hydrogen and hydroxy;

(C) $R^5$ is selected from the group consisting of hydrogen and alkyl;

(D) M is —E—$(CR^{19}R^{19'})_w R^{20}$ where (1) w is from 0 to about 4;

(2) E is selected from a —O—; —$S_x$— where x is from 0 to 2; and —$NR^{21}$— where $R^{21}$ is selected from hydrogen, alkyl, alkenyl, heteroalkyl, aryl, heteroaryl, cycloalkyl, and heterocycloalkyl, or $R^{21}$ can join with $R^{20}$ to form a ring with 5 to 8 members and 1 to 3 heteroatoms;

(3) each $R^{19}$ and $R^{19'}$ is hydrogen;

(4) $R^{20}$ is selected from hydrogen, alkyl, alkenyl, alkynyl, heteroalkl, haloalkyl, cycloalkyl, heterocycloalkyl, aryl, and heteroaryl; and (E) Z is

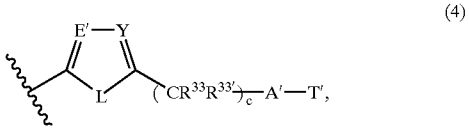

(4)

where a. E' and Y are —CH—;

b. L is —$C(R^{35})$=$C(R^{35'})$—, where $R^{35}$ and $R^{35'}$ each is hydrogen;

(c) c is 0;

(d) A' is selected from covalent bond, —O— and —S—; and (e) T' is —$(CR^{37}R^{37'})_e$—$R^{38}$ where c is 0; and $R^{38}$ is selected from hydrogen, alkyl, alkenyl, alkynyl, halogen, heteroalkyl, haloalkyl, aryl, heteroaryl, cycloalkyl, and hererocycloalkyl;

or an optical isomer, diastercomer or enantiomer for Formula (I), or a pharmaceutically-acceptable salt, or biohydrolyzable amide, ester, or imide thereof.

2. The compound of claim 1, wherein $R^{38}$ is selected from alkyl, heteroalkyl, aryl, heteroaryl, cycloalkyl and heterocycloalkyl.

3. The compound of claim 2, wherein $R^{38}$ is selected from heteroaryl and heterocycloalkyl.

4. The compound of claim 3, wherein the heteroaryl is substituted from the group consisting of halo, cyano, nitro, hydroxy, carboxy, amino, acylamino, alkyl, heteroalkyl, haloalkyl, phenyl, alkoxy, aryloxy, heteroaryloxy, and combinations thereof.

5. The compound of claim 3, wherein the heterocycloalkyl is substituted from the group consisting of halo, cyano, hydroxy, carboxy, keto, thioketo, amino, acylamino, acyl, amido, alkyl, heteroalkyl, haloalkyl, phenyl, alkoxy, aryloxy, and combinations thereof.

6. The compound of claim 1, wherein Z is 4-methoxyphenyl.

7. The compound of claim 1, wherein $R^3$, T and $R^5$ are each hydrogen.

8. The compound of claim 1, wherein the compound is selected from the group consisting of:

2-[(4'-Methoxy[1,1'-biphenyl]-4-yl)sulfonyl]amino-4-hydroxy-5-[(2-thiazolyl)thio]-pentanoic acid;

2-[(4'-(Methylthio)[1,1'-biphenyl]-4-yl)sulfonyl]amino-4-hydroxy-5-[(2-thiazolyl)thio]-pentanoic acid;

2-[(4'-Phenoxy[1,1'-biphenyl]-4-yl)sulfonyl]amino-4-hydroxy-5-[(2-thiazolyl)thio]-pentanoic acid;

2-[(4'-(2-Methoxyethoxy)[1,1'-biphenyl]-4-yl)sulfonyl]amino-4-hydroxy-5-[(2-thiazolyl)thio]-pentanoic acid;

2-[(4'-(2-(1-Pyrrolidinyl)ethoxy)[1,1'-biphenyl]-4-yl)sulfonyl]amino-4-hydroxy-5-[(2-thiazolyl)thio]-pentanoic acid;

2-[(1,1':4',1''-Terphenyl]-4-yl)sulfonyl]amino-4-hydroxy-5-[(2-thiazolyl)thio]-pentanoic acid;

2-[(3',4'-(Methylenedioxy)[1,1'-biphenyl]-4-yl)sulfonyl]amino-4-hydroxy-5-[(2-thiazolyl)thio]-pentanoic acid;

2-[(3'-Ethoxy[1,1'-biphenyl]-4-yl)sulfonyl]amino-4-hydroxy-5-[(2-thiazolyl)thio]-pentanoic acid;

2-[[4-[(4-Methoxyphenyl)ethynyl]phenyl]sulfonyl]amino-4-hydroxy-5-[(2-thiazolyl)thio]-pentanoic acid;

2-[[4-[(4-Methylphenyl)ethynyl]phenyl]sulfonyl]amino-4-hydroxy-5-[(2-thiazolyl)thio]-pentanoic acid;

2-[[4-(Phenylazo)phenyl]sulfonyl]amino-4-hydroxy-5-[(2-thiazolyl)thio]-pentanoic acid;

2-[(4'-Chloro[1,1'-biphenyl]-4-yl)sulfonyl]amino-4-hydroxy-5-[2-thiazolylthio]-pentanoic acid;
2-[(4'-Bromo[1,1'-biphenyl]-4-yl)sulfonyl]amino-4-hydroxy-5-[2-thiazolylthio]-pentanoic acid;
2-[(4'-Trifluoromethyl[1,1'-biphenyl]-4-yl)sulfonyl]amino-4-hydroxy-5-[2-thiazolylthio]-pentanoic acid;
2-[(4'-Methoxy[1,1'-biphenyl]-4-yl)sulfonyl]amino-4-hydroxy-5-(phenylthio)-pentanoic acid;
2-[[(1,1'-biphenyl)-4-yl]sulfonyl]amino-4-hydroxy-5-(phenylthio)-pentanoic acid;
2-[(4'-Methoxy[1,1'-biphenyl]-4-yl)sulfonyl]amino-4-hydroxy-5-(benzylthio)-pentanoic acid;
2-[(4'-Methoxy[1,1'-biphenyl]-4-yl)sulfonyl]amino-4-hydroxy-5-[(benzyl)sulfonyl]-pentanoic acid;
2-[(4'-Methoxy[1,1'-biphenyl]-4-yl)sulfonyl]amino-4-hydroxy-5-(phenylamino)-pentanoic acid;
2-[(4'-Methoxy[1,1'-biphenyl]-4-yl)sulfonyl]amino-4-hydroxy-5-[(1H-1,2,4-triazol-3-yl)thio]-pentanoic acid;
2-[(4'-Methoxy[1,1'-biphenyl]-4-yl)sulfonyl]amino-4-hydroxy-5-(phenylamino)-pentanoic acid;
2-[(4'-Methoxy[1,1'-biphenyl]-4-yl)sulfonyl]amino-4-hydroxy-5-[(2-imidazolyl)thio]-pentanoic acid;
2-[(4'-Methoxy[1,1'-biphenyl]-4-yl)sulfonyl]amino-4-hydroxy-5-[[2-(5-methylbenzimidazolyl)]thio]-pentanoic acid;
2-[(4'-Methoxy[1,1'-biphenyl]-4-yl)sulfonyl]amino-4-hydroxy-5-[(4(3H)-quinazolinonyl)thio]-pentanoic acid;
2-[(4'-Methoxy[1,1'-biphenyl]-4-yl)sulfonyl]amino-4-hydroxy-5-[(6-ethoxy-2-benzothiazolyl)thio]-pentanoic acid;
2-[(4'-Methoxy[1,1'-biphenyl]-4-yl)sulfonyl]amino-4-hydroxy-5-[2-benzothiazolylthio]-pentanoic acid;
2-[(4'-Methoxy[1,1'-biphenyl]-4-yl)sulfonyl]amino-4-hydroxy-5-[2-benzoxazolylthio]-pentanoic acid;
2-[(4'-Methoxy[1,1'-biphenyl]-4-yl)sulfonyl]amino-4-hydroxy-5-[2-benzimidazolylthio]-pentanoic acid;
2-[(4'-Methoxy[1,1'-biphenyl]-4-yl)sulfonyl]amino-4-hydroxy-5-[2-(1-methyl-1H-imidazol-2-yl)thio]-pentanoic acid;
2-[(4'-Methoxy[1,1'-biphenyl]-4-yl)sulfonyl]amino-4-hydroxy-5-[(1-methyl-1H-tetrazol-5-yl)thio]-pentanoic acid;
2-[(4'-Methoxy[1,1'-biphenyl]-4-yl)sulfonyl]amino-4-hydroxy-5-[(5-methyl-1,3,4-thiadiazol-2-yl)thio]-pentanoic acid;
2-[(4'-Methoxy[1,1'-biphenyl]-4-yl)sulfonyl]amino-4-hydroxy-5-[(4-methyl-4(H)-1,2,4-triazol-3-yl)thio]-pentanoic acid;
2-[(4'-Methoxy[1,1'-biphenyl]-4-yl)sulfonyl]amino-4-hydroxy-5-[(5-(methylthio)-1,3,4-thiadiazol-2-yl)thio]-pentanoic acid;
2-[(4'-Methoxy[1,1'-biphenyl]-4-yl)sulfonyl]amino-4-hydroxy-5-[2-thienylthio]-pentanoic acid;
2-[(4'-Methoxy[1,1'-biphenyl]-4-yl)sulfonyl]amino-4-hydroxy-5-[(5-phenyl-1,3,4-oxadiazol-2-yl)thio]-pentanoic acid;
2-[(4'-Methoxy[1,1'-biphenyl]-4-yl)sulfonyl]amino-4-hydroxy-5-[(1(4-methoxyphenyl)-1H-tetrazol-1-yl)thio]-pentanoic acid;
2-[(4'-Methoxy[1,1'-biphenyl]-4-yl)sulfonyl]amino-4-hydroxy-5-[(6-chloro-2-benzoxazolyl)thio]-pentanoic acid;
2-[(4'-Methoxy[1,1'-biphenyl]-4-yl)sulfonyl]amino-4-hydroxy-5-[[3-(methylthio)-1,2,4-thiadiazol-5-yl]thio]-pentanoic acid;
2-[(4'-Methoxy[1,1'-biphenyl]-4-yl)sulfonyl]amino-4-hydroxy-5-[[5-(4-pyridinyl)-1,3,4-oxadiazol-2-yl]thio]-pentanoic acid;
2-[(4'-Methoxy[1,1'-biphenyl]-4-yl)sulfonyl]amino-4-hydroxy-5-[(5-methoxybenzothiazoly-2-yl)thio]-pentanoic acid;
2-[(4'-Methoxy[1,1'-biphenyl]-4-yl)sulfonyl]amino-4-hydroxy-5-[(5-methoxy-benzimidazol-2-yl)thio]-pentanoic acid;
2-[(4'-Methoxy[1,1'-biphenyl]-4-yl)sulfonyl]amino-4-hydroxy-5-[(5-phenyl-1H-1,2,4-triazol-3-yl)thio]-pentanoic acid;
2-[(4'-Methoxy[1,1'-biphenyl]-4-yl)sulfonyl]amino-4-hydroxy-5-[(2-methyl-3-furanyl)thio]-pentanoic acid;
2-[(4'-Methoxy[1,1'-biphenyl]-4-yl)sulfonyl]amino-4-hydroxy-5-[(4-methoxyphenyl)thio]-pentanoic acid;
2-[(4'-Methoxy[1,1'-biphenyl]-4-yl)sulfonyl]amino-4-hydroxy-5-[pyrimidin-2-ylthio]-pentanoic acid;
2-[(4'-Methoxy[1,1'-biphenyl]-4-yl)sulfonyl]amino-4-hydroxy-5-[4,6-dimethylpyrimidin-2-ylthio]-pentanoic acid;
2-[(4'-Methoxy[1,1'-biphenyl]-4-yl)sulfonyl]amino-4-hydroxy-5-[pyridin-2-ylthio]-pentanoic acid;
2-[(4'-Methoxy[1,1'-biphenyl]-4-yl)sulfonyl]amino-4-hydroxy-5-[purin-2-ylthio]-pentanoic acid;
2-[(4'-Methoxy[1,1'-biphenyl]-4-yl)sulfonyl]amino-4-hydroxy-5-[4-methylcoumarin-7-ylthio]-pentanoic acid;
2-[(4'-Methoxy[1,1'-biphenyl]-4-yl)sulfonyl]amino-4-hydroxy-5-[[(4-methoxyphenyl)methyl]thio]-pentanoic acid;
2-[(4'-Methoxy[1,1'-biphenyl]-4-yl)sulfonyl]amino-4-hydroxy-5-[[(4-fluorophenyl)methyl]thio]-pentanoic acid;
2-[(4'-Methoxy[1,1'-biphenyl]-4-yl)sulfonyl]amino-4-hydroxy-5-[furfurylthio]-pentanoic acid;
2-[(4'-Methoxy[1,1'-biphenyl]-4-yl)sulfonyl]amino-4-hydroxy-5-[(2-thienyl)methylthio]-pentanoic acid;
2-[(4'-Methoxy[1,1'-biphenyl]-4-yl)sulfonyl]amino-4-hydroxy-5-phenoxypentanoic acid;
2-[(4'-Methoxy[1,1'-biphenyl]-4-yl)sulfonyl]amino-4-hydroxy-5-[pyridin-3-yloxy]-pentanoic acid;
2-[(4'-Methoxy[1,1'-biphenyl]-4-yl)sulfonyl]amino-4-hydroxy-5-[pyrimidin-2-yloxy]-pentanoic acid;
2-[(4'-Methoxy[1,1'-biphenyl]-4-yl)sulfonyl]amino-4-hydroxy-4-methyl-5-[(1-N-methyl-imidazol-2-yl-thio)-methyl]-pentanoic acid;
2-[(4'-Methoxy[1,1'-biphenyl]-4-yl)sulfonyl]amino-3-phenylmethoxy-4-hydroxy-5-[(2-thiazolyl)thio]-pentanoic acid;
2-[(4'-Thiomethoxy[1,1'-biphenyl]-4-yl)sulfonyl]amino-3-phenylmethoxy4-hydroxy-5-[(2-thiazolyl)thio]-pentanoic acid;
2-[(4'-Methoxy[1,1'-biphenyl]-4-yl)sulfonyl]amino-3,4-dihydroxy-5-[(2-thiazolyl)thio]-pentanoic acid;
2-[(4'-Methoxy[1,1'-biphenyl]-4-yl)sulfonyl]amino-3,4-dihydroxy-5-[(4-methyl-4(H)-1,2,4-triazol-3-yl)thio]-pentanoic acid;
2-[(4'-Methoxy[1,1'-biphenyl]-4-yl)sulfonyl]amino-3,4-dihydroxy-5-[(4-methyl-4(H)-1,2,4-triazol-3-yl)thio]-pentanoic acid;
2-[(4'-Methoxy[1,1'-biphenyl]-4-yl)sulfonyl]amino-4-hydroxy-4-methyl-5-[(3-trifluoromethylpyridin-2-yl)-thiomethyl]-pentanoic acid;
2-[(4'-Methoxy[1,1'-biphenyl]-4-yl)sulfonyl]amino-4-hydroxy-5-[(3-trifluoromethyl)-2-pyridyl-thio]-pentanoic acid;
2-[(4'-Methoxy[1,1'-biphenyl]-4-yl)sulfonyl]-N-methyl-amino-4-hydroxy-5-phenylthio)-pentanoic acid;
2-[(4'-Methoxy[1,1'-biphenyl]-4-yl)sulfonyl]amino-3-phenylmethoxy-4-hydroxy-5-[(2-thiazolyl)thio]-pentanoic acid;

2-[(4'-Thiomethoxy[1,1'-biphenyl]-4-yl)sulfonyl]amino-3-phenylmethoxy-4-hydroxy-5-[(2-thiazolyl)thio]-pentanoic acid;

2-[(4'-Methoxy[1,1'-biphenyl]-4-yl)sulfonyl]amino-3,4-dihydroxy-5-[(2-thiazolyl)thio]-pentanoic acid;

2-[(4'-Methoxy[1,1'-biphenyl]-4-yl)sulfonyl]amino-3,4-dihydroxy-5-[(4-methyl-4(H)-1,2,4-triazol-3-yl)thio]-pentanoic acid;

2-[(4'-Methoxy-[1,1'-biphenyl]-4-yl)-sulfonyl]-amino-3-(2-phenoxymethyl-[1,3]dioxan-2-yl)-propionic acid;

2-[(4'-Bromo-[1,1'-biphenyl]-4-yl)-sulfonyl]-amino-3-(2-phenoxymethyl-[1,3]dioxan-2-yl)-propionic acid;

2-[(4'-Methoxy-[1,1'-biphenyl]-4-yl)-sulfonyl]-amino-3-(2-thiophenoxymethyl-[1,3]dioxan-2-yl)-propionic acid;

2-[(4'-Methoxy-[1,1'-biphenyl]-4-yl)-sulfonyl]-amino-3-[2-(2-oxo-azepan-1-ylmethyl)-[1,3]dioxan-2-yl]-propionic acid, and 2-[(4'-Methoxy-[1,1'-biphenyl]-4-yl)-sulfonyl]-amino-3-(2-phenoxyethyl-[1,3]dioxan-2-yl)-propionic acid.

9. A pharmaceutical composition comprising:
(a) a safe and effective amount of a compound of claim 1; and
(b) a pharmaceutically-acceptable carrier.

10. A method of preventing or treating a metalloprotease related disorder in a mammalian subject, the method comprising administering to said subject a safe and effective amount of a compound of claim 1.

11. The method of claim 10, wherein said metalloprotease related disorder is selected from the group consisting of arthritis, cancer, cardiovascular disorder, skin disorder, ocular disorder, inflammation and gum disease.

12. The method of claim 11, wherein the disorder is arthritis, and is chosen from the group consisting of osteoarthritis and rheumatoid arthritis.

13. The method of claim 11, wherein the disorder is cancer.

14. The method of claim 11, wherein the disorder is cardiovascular disorder chosen from the group consisting of dilated cardiomyopathy, congestive heart failure, atherosclerosis, plaque rupture, reperfusion injury, ischemia, chronic obstructive pulmonary disease, angioplasty restenosis and aortic aneurysm.

15. The method of claim 11, wherein the disorder is an ocular disorder, and is chosen from the group consisting of corneal ulceration, lack of corneal healing, macular degeneration, retinopathy, and pterygium.

16. The method of claim 11, wherein the disorder is gum disease, and is chosen from the group consisting of periodontal disease and gingivitis.

17. The method of claim 11, wherein the disorder is skin disorder chosen from the group consisting of wrinkle, U.V. skin damage, epidermolysis bullosa, psoriasis, sclerodema, atopic dermatitis and scarring.

18. The method of claim 10, wherein said metalloprotease related disorder is chosen from the group comprising joint replacements and dental prosthesis.

19. The method claim 11, wherein said inflammatory condition is chosen from the group consisting of inflammatory bowel disease, Crohn's Disease, ulcerative colitis, pancreatitis, diverticulitis, acne inflammation, bronchitis, arthritis and asthma.

20. The method claim 10, wherein said metalloprotease related disorder is multiple sclerosis.

21. The method of claim 10, wherein said metalloprotease related disorder is musculoskeletal disease or cachexia.

* * * * *

UNITED STATES PATENT AND TRADEMARK OFFICE
CERTIFICATE OF CORRECTION

PATENT NO. : 6,566,381 B1
DATED : May 20, 2003
INVENTOR(S) : Menyan Cheng et al.

It is certified that error appears in the above-identified patent and that said Letters Patent is hereby corrected as shown below:

Column 52,
Lines 1 and 5, delete "[" and insert -- ]- --.

Column 58,
Line 31, delete "[" and insert -- ]- --.

Column 60,
Line 22, delete "[-" and insert -- ]- --.

Column 64,
Line 58, delete "4penenoic" and insert -- 4-pentenoic --

Signed and Sealed this

Twenty-third Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,566,381 B1
DATED : May 20, 2003
INVENTOR(S) : Menyan Cheng et al.

It is certified that error appears in the above-identified patent and that said Letters Patent is hereby corrected as shown below:

Column 74,
Delete lines 56-57
Delete lines 62-67

Column 76,
Delete lines 46-48
Delete lines 54-56

Column 77,
Delete lines, 1-3
Delete lines, 6-8
Delete lines, 9-19

Signed and Sealed this

Fifth Day of April, 2005

JON W. DUDAS
*Director of the United States Patent and Trademark Office*

UNITED STATES PATENT AND TRADEMARK OFFICE
CERTIFICATE OF CORRECTION

PATENT NO. : 6,566,381 B1
DATED : May 20, 2003
INVENTOR(S) : Menyan Cheng et al.

It is certified that error appears in the above-identified patent and that said Letters Patent is hereby corrected as shown below:

Column 75,
Lines 18-19, delete.

Column 76,
Lines 43-45 and 65-67, delete.

Column 77,
Lines 4-5, delete.

Signed and Sealed this

Twentieth Day of September, 2005

JON W. DUDAS
*Director of the United States Patent and Trademark Office*

UNITED STATES PATENT AND TRADEMARK OFFICE
CERTIFICATE OF CORRECTION

PATENT NO. : 6,566,381 B1 Page 1 of 1
DATED : May 20, 2003
INVENTOR(S) : Menyan Cheng et al.

It is certified that error appears in the above-identified patent and that said Letters Patent is hereby corrected as shown below:

Column 75,
Delete lines 18-19.

Column 76,
Delete lines 43-45.
Delete lines 65-67.

Column 77,
Delete lines 4-5.

Signed and Sealed this

Eleventh Day of April, 2006

JON W. DUDAS
*Director of the United States Patent and Trademark Office*